US012681022B2

(12) United States Patent
Montaner Villalonga

(10) Patent No.: US 12,681,022 B2
(45) Date of Patent: Jul. 14, 2026

(54) METHOD FOR SELECTING A PATIENT FOR A REPERFUSION THERAPY

(71) Applicant: FUNDACIÓ HOSPITAL UNIVERSITARI VALL D'HEBRON—INSTITUT DE RECERCA, Barcelona (ES)

(72) Inventor: Joan Montaner Villalonga, Barcelona (ES)

(73) Assignee: FUNDACIÓ HOSPITAL UNIVERSITARI VALL D'HEBRON—INSTITUT DE RECERCA, Barcelona (ES)

( * ) Notice: Subject to any disclaimer, the term of this patent is extended or adjusted under 35 U.S.C. 154(b) by 1276 days.

(21) Appl. No.: 17/611,874

(22) PCT Filed: May 15, 2020

(86) PCT No.: PCT/EP2020/063726
§ 371 (c)(1),
(2) Date: Nov. 16, 2021

(87) PCT Pub. No.: WO2020/229691
PCT Pub. Date: Nov. 19, 2020

(65) Prior Publication Data
US 2022/0381794 A1 Dec. 1, 2022

(30) Foreign Application Priority Data
May 16, 2019 (EP) ..................................... 19382384

(51) Int. Cl.
*G01N 33/68* (2006.01)

(52) U.S. Cl.
CPC ..... *G01N 33/6893* (2013.01); *G01N 2333/58* (2013.01); *G01N 2800/2871* (2013.01); *G01N 2800/52* (2013.01)

(58) Field of Classification Search
CPC .................. G01N 33/6893; G01N 2800/2871
USPC ....................................................... 435/7.1
See application file for complete search history.

(56) References Cited

U.S. PATENT DOCUMENTS

| | | | |
|---|---|---|---|
| 10,520,513 B2 * | 12/2019 | Montaner Viallonga | ..................... G01N 33/48 |
| 11,726,100 B2 * | 8/2023 | Gaude | .................. B05B 7/0884 435/7.1 |
| 2005/0181386 A1 | 8/2005 | Diamond et al. | |
| 2013/0189243 A1 * | 7/2013 | Barr | ..................... C12Q 1/6883 435/6.12 |

FOREIGN PATENT DOCUMENTS

| | | | | |
|---|---|---|---|---|
| WO | WO-2016087611 A1 * | 6/2016 | ............. | G01N 33/48 |
| WO | WO 2018/160548 A1 | 9/2018 | | |

OTHER PUBLICATIONS

Bustamante et al., Blood Biomarkers for the Early Diagnosis of Stroke, The Stroke-Chip Study, Stroke. 2017;48: 2419-2425. (Year: 2017).*
Llombart et al., Plasmatic retinol-binding protein 4 and glial fibrillary acidic protein as biomarkers to differentiate ischemic stroke and intracerebral hemorrhage, J. Neurochem. (2016) 136, 416-424. (Year: 2015).*
Sheth et al., Drip and Ship Thrombolytic Therapy for Acute Ischemic Stroke, Stroke. 2015;46:732-739. (Year: 2015).*
Llombart et al., Plasmatic retinol-binding protein 4 and glial fibrillary acidic protein as biomarkers to differentiate ischemic stroke and intracerebral hemorrhage, J. Neurochem, (2016) 136, 416-424. (Year: 2016).*
International Search Report and Written Opinion mailed Nov. 16, 2020 for Application No. PCT/EP2020/063726, 24 pages.
Adams, et al: "Baseline NIH Stroke Scale score strongly predicts outcome after stroke: A report of the Trial of Org 10172 in Acute Stroke Treatment (TOAST)", Neurology; Jul. 13, 1999; vol. 53(1), pp. 126-131.
Altschul, et al: BLASTManual, Basic Local Alignment Search Tool, Journal of Molecular Biology 1990; vol. 215, pp. 403-410.
Bustamante, et al: "Blood Biomarkers for the Early Diagnosis of Stroke—The Stroke-Chip Study", Stoke; Sep. 1, 2017; vol. 49(9), p. 2419-2425.
Crowe, et al: "The Cincinnati Prehospital Stroke Scale Compared to Stroke Severity Tools for Large Vessel Occlusion Stroke Prediction", Prehospital Emergency Care; Feb. 25, 2020; pp. 1-27.
Gandhi, et al: "Neuroendovascular management of emergent large vessel occlusion: update on the technical aspects and standards of practice by the Standards and Guidelines Committee of the Society of Neurointerventional Surgery", Journal of Neurointerventional Surgery; Jan. 11, 2018 (online); vol. 10, pp. 315-320.
Jolliffe, "Principal Component Analysis, second edition—Springer Series in Statistics", Springer 2002; ISBN 0-387-95442-2; 518 pages.
Kunz, et al: "Effects of Ultraearly Intravenous Thrombolysis on Outcomes in Ischemic Stroke", The STEMO (Stroke Emergency Mobile) Group Circulation; May 2, 2017; vol. 135(18), pp. 1765-1767.
Lakomkin, et al: "Prevalence of large vessel occlusion in patients presenting with acute ischemic stroke: a 10-year systematic review of the literature", Journal of Neurointerventional Surgery 2019; vol. 11; pp. 241-245.

(Continued)

*Primary Examiner* — Gregory S Emch
*Assistant Examiner* — Omar Ramadan
(74) *Attorney, Agent, or Firm* — Squire Patton Boggs (US) LLP

(57) ABSTRACT

The invention relates to a method for selecting a patient suffering stroke for a reperfusion therapy based on determining the level of retinol binding protein-4 (RBP4) and N-terminal fragment of B-type natriuretic peptide (NT-proBNP) in an isolated sample of said patient. The invention also relates to a method of differentiating ischemic stroke from haemorrhagic stroke and to kits comprising reagents to carry out the methods.

6 Claims, 6 Drawing Sheets

Specification includes a Sequence Listing.

(56)          References Cited

OTHER PUBLICATIONS

Montaner, et al: "Etiologic Diagnosis of Ischemic Stroke Subtypes With Plasma Biomarkers", Stroke 2008, vol. 39, pp. 2280-2287.
Rai, et al: "A population-based incidence of acute large vessel occlusions and thrombectomy eligible patients indicates significant potential for growth of endovascular stroke therapy in the USA", Journal of Neurointerventional Surger; Jul. 15, 2016 (online); vol. 9, pp. 722-726; doi:10.1136/neurintsurg-2016-012515.
Reynolds, et al: "Early Biomarkers of Stroke", Clinical Chemistry 2003; vol. 49(10), pp. 1733-1739.
Tsivgoulis, et al: "Intensive blood pressure reduction in acute intracerebral hemorrhage—A meta analysis", Neurology; Sep. 19, 2014 (online); vol. 83, pp. 1-7.
Vanacker, et al: "Prediction of large vessel occlusions in acute stroke: National institute of Health Stroke Scale is hard to beat", Journal of Critical Care Medicine; Jun. 2016; vol. 44(6), pp. e336-343.
Waqas, et al: "Effect of definition and methods on estimates of prevalence of large vessel occlusion in acute ischemic stroke: a systematic review and meta-analysis", Journal of Neurointerventional Surgery; Mar. 2020; vol. 12(3), pp. 260-265.

* cited by examiner (A)

(B)

(C)
Log₁₀(NT-PROBNP)
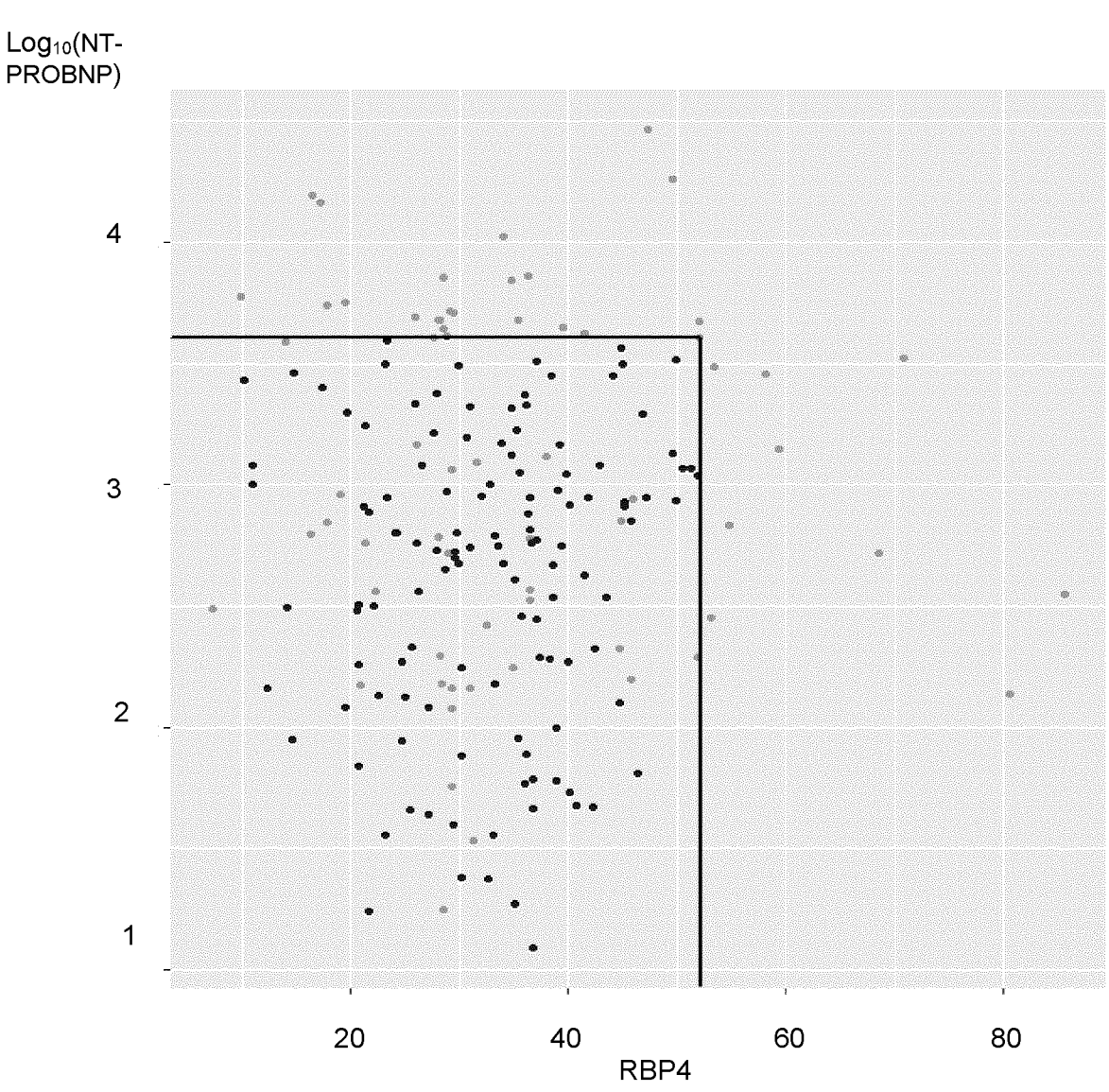
RBP4
Cont. FIG. 1

(A)

(B)

SEQUENCE LISTING

<160> NUMBER OF SEQ ID NOS: 5

<210> SEQ ID NO 1
<211> LENGTH: 562
<212> TYPE: PRT
<213> ORGANISM: Homo sapiens

<400> SEQUENCE: 1

```
Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Arg Ser Tyr Gln Val Ile Cys Arg Asp Glu Lys Thr Gln Met
        35                  40                  45

Ile Tyr Gln Gln His Gln Ser Trp Leu Arg Pro Val Leu Arg Ser Asn
    50                  55                  60

Arg Val Glu Tyr Cys Trp Cys Asn Ser Gly Arg Ala Gln Cys His Ser
65                  70                  75                  80

Val Pro Val Lys Ser Cys Ser Glu Pro Arg Cys Phe Asn Gly Gly Thr
                85                  90                  95

Cys Gln Gln Ala Leu Tyr Phe Ser Asp Phe Val Cys Gln Cys Pro Glu
            100                 105                 110

Gly Phe Ala Gly Lys Cys Cys Glu Ile Asp Thr Arg Ala Thr Cys Tyr
```

-continued

```
              115                   120                   125

Glu Asp Gln Gly Ile Ser Tyr Arg Gly Thr Trp Ser Thr Ala Glu Ser
    130                   135                   140

Gly Ala Glu Cys Thr Asn Trp Asn Ser Ser Ala Leu Ala Gln Lys Pro
145                   150                   155                   160

Tyr Ser Gly Arg Arg Pro Asp Ala Ile Arg Leu Gly Leu Gly Asn His
                165                   170                   175

Asn Tyr Cys Arg Asn Pro Asp Arg Asp Ser Lys Pro Trp Cys Tyr Val
                180                   185                   190

Phe Lys Ala Gly Lys Tyr Ser Ser Glu Phe Cys Ser Thr Pro Ala Cys
            195                   200                   205

Ser Glu Gly Asn Ser Asp Cys Tyr Phe Gly Asn Gly Ser Ala Tyr Arg
    210                   215                   220

Gly Thr His Ser Leu Thr Glu Ser Gly Ala Ser Cys Leu Pro Trp Asn
225                   230                   235                   240

Ser Met Ile Leu Ile Gly Lys Val Tyr Thr Ala Gln Asn Pro Ser Ala
                245                   250                   255

Gln Ala Leu Gly Leu Gly Lys His Asn Tyr Cys Arg Asn Pro Asp Gly
            260                   265                   270

Asp Ala Lys Pro Trp Cys His Val Leu Lys Asn Arg Arg Leu Thr Trp
            275                   280                   285

Glu Tyr Cys Asp Val Pro Ser Cys Ser Thr Cys Gly Leu Arg Gln Tyr
    290                   295                   300

Ser Gln Pro Gln Phe Arg Ile Lys Gly Gly Leu Phe Ala Asp Ile Ala
305                   310                   315                   320

Ser His Pro Trp Gln Ala Ala Ile Phe Ala Lys His Arg Arg Ser Pro
                325                   330                   335

Gly Glu Arg Phe Leu Cys Gly Gly Ile Leu Ile Ser Ser Cys Trp Ile
            340                   345                   350

Leu Ser Ala Ala His Cys Phe Gln Glu Arg Phe Pro Pro His His Leu
            355                   360                   365

Thr Val Ile Leu Gly Arg Thr Tyr Arg Val Val Pro Gly Glu Glu Glu
    370                   375                   380

Gln Lys Phe Glu Val Glu Lys Tyr Ile Val His Lys Glu Phe Asp Asp
385                   390                   395                   400

Asp Thr Tyr Asp Asn Asp Ile Ala Leu Leu Gln Leu Lys Ser Asp Ser
                405                   410                   415

Ser Arg Cys Ala Gln Glu Ser Ser Val Val Arg Thr Val Cys Leu Pro
            420                   425                   430

Pro Ala Asp Leu Gln Leu Pro Asp Trp Thr Glu Cys Glu Leu Ser Gly
            435                   440                   445

Tyr Gly Lys His Glu Ala Leu Ser Pro Phe Tyr Ser Glu Arg Leu Lys
    450                   455                   460

Glu Ala His Val Arg Leu Tyr Pro Ser Ser Arg Cys Thr Ser Gln His
465                   470                   475                   480

Leu Leu Asn Arg Thr Val Thr Asp Asn Met Leu Cys Ala Gly Asp Thr
                485                   490                   495

Arg Ser Gly Gly Pro Gln Ala Asn Leu His Asp Ala Cys Gln Gly Asp
            500                   505                   510

Ser Gly Gly Pro Leu Val Cys Leu Asn Asp Gly Arg Met Thr Leu Val
            515                   520                   525

Gly Ile Ile Ser Trp Gly Leu Gly Cys Gly Gln Lys Asp Val Pro Gly
    530                   535                   540
```

```
Val Tyr Thr Lys Val Thr Asn Tyr Leu Asp Trp Ile Arg Asp Asn Met
545                 550                 555                 560

Arg Pro

<210> SEQ ID NO 2
<211> LENGTH: 527
<212> TYPE: PRT
<213> ORGANISM: Artificial
<220> FEATURE:
<223> OTHER INFORMATION: Modified human tissue plasminogen activator
      (Tenecteplase or TNK)

<400> SEQUENCE: 2

Ser Tyr Gln Val Ile Cys Arg Asp Glu Lys Thr Gln Met Ile Tyr Gln
1               5                   10                  15

Gln His Gln Ser Trp Leu Arg Pro Val Leu Arg Ser Asn Arg Val Glu
            20                  25                  30

Tyr Cys Trp Cys Asn Ser Gly Arg Ala Gln Cys His Ser Val Pro Val
            35                  40                  45

Lys Ser Cys Ser Glu Pro Arg Cys Phe Asn Gly Gly Thr Cys Gln Gln
    50                  55                  60

Ala Leu Tyr Phe Ser Asp Phe Val Cys Gln Cys Pro Glu Gly Phe Ala
65                  70                  75                  80

Gly Lys Cys Cys Glu Ile Asp Thr Arg Ala Thr Cys Tyr Glu Asp Gln
                85                  90                  95

Gly Ile Ser Tyr Arg Gly Asn Trp Ser Thr Ala Glu Ser Gly Ala Glu
                100                 105                 110

Cys Thr Asn Trp Gln Ser Ser Ala Leu Ala Gln Lys Pro Tyr Ser Gly
            115                 120                 125

Arg Arg Pro Asp Ala Ile Arg Leu Gly Leu Gly Asn His Asn Tyr Cys
            130                 135                 140

Arg Asn Pro Asp Arg Asp Ser Lys Pro Trp Cys Tyr Val Phe Lys Ala
145                 150                 155                 160

Gly Lys Tyr Ser Ser Glu Phe Cys Ser Thr Pro Ala Cys Ser Glu Gly
                165                 170                 175

Asn Ser Asp Cys Tyr Phe Gly Asn Gly Ser Ala Tyr Arg Gly Thr His
                180                 185                 190

Ser Leu Thr Glu Ser Gly Ala Ser Cys Leu Pro Trp Asn Ser Met Ile
            195                 200                 205

Leu Ile Gly Lys Val Tyr Thr Ala Gln Asn Pro Ser Ala Gln Ala Leu
    210                 215                 220

Gly Leu Gly Lys His Asn Tyr Cys Arg Asn Pro Asp Gly Asp Ala Lys
225                 230                 235                 240

Pro Trp Cys His Val Leu Lys Asn Arg Arg Leu Thr Trp Glu Tyr Cys
                245                 250                 255

Asp Val Pro Ser Cys Ser Thr Cys Gly Leu Arg Gln Tyr Ser Gln Pro
                260                 265                 270

Gln Phe Arg Ile Lys Gly Gly Leu Phe Ala Asp Ile Ala Ser His Pro
            275                 280                 285

Trp Gln Ala Ala Ile Phe Ala Ala Ala Ala Ser Pro Gly Glu Arg
    290                 295                 300

Phe Leu Cys Gly Gly Ile Leu Ile Ser Ser Cys Trp Ile Leu Ser Ala
305                 310                 315                 320

Ala His Cys Phe Gln Glu Arg Phe Pro Pro His His Leu Thr Val Ile
                325                 330                 335
```

-continued

```
Leu Gly Arg Thr Tyr Arg Val Val Pro Gly Glu Glu Glu Gln Lys Phe
            340             345             350

Glu Val Glu Lys Tyr Ile Val His Lys Glu Phe Asp Asp Asp Thr Tyr
            355             360             365

Asp Asn Asp Ile Ala Leu Leu Gln Leu Lys Ser Asp Ser Ser Arg Cys
    370             375             380

Ala Gln Glu Ser Ser Val Val Arg Thr Val Cys Leu Pro Pro Ala Asp
385             390             395             400

Leu Gln Leu Pro Asp Trp Thr Glu Cys Glu Leu Ser Gly Tyr Gly Lys
            405             410             415

His Glu Ala Leu Ser Pro Phe Tyr Ser Glu Arg Leu Lys Glu Ala His
            420             425             430

Val Arg Leu Tyr Pro Ser Ser Arg Cys Thr Ser Gln His Leu Leu Asn
            435             440             445

Arg Thr Val Thr Asp Asn Met Leu Cys Ala Gly Asp Thr Arg Ser Gly
    450             455             460

Gly Pro Gln Ala Asn Leu His Asp Ala Cys Gln Gly Asp Ser Gly Gly
465             470             475             480

Pro Leu Val Cys Leu Asn Asp Gly Arg Met Thr Leu Val Gly Ile Ile
            485             490             495

Ser Trp Gly Leu Gly Cys Gly Gln Lys Asp Val Pro Gly Val Tyr Thr
            500             505             510

Lys Val Thr Asn Tyr Leu Asp Trp Ile Arg Asp Asn Met Arg Pro
            515             520             525

<210> SEQ ID NO 3
<211> LENGTH: 201
<212> TYPE: PRT
<213> ORGANISM: Homo sapiens

<400> SEQUENCE: 3

Met Lys Trp Val Trp Ala Leu Leu Leu Leu Ala Ala Leu Gly Ser Gly
1               5               10              15

Arg Ala Glu Arg Asp Cys Arg Val Ser Ser Phe Arg Val Lys Glu Asn
            20              25              30

Phe Asp Lys Ala Arg Phe Ser Gly Thr Trp Tyr Ala Met Ala Lys Lys
            35              40              45

Asp Pro Glu Gly Leu Phe Leu Gln Asp Asn Ile Val Ala Glu Phe Ser
    50              55              60

Val Asp Glu Thr Gly Gln Met Ser Ala Thr Ala Lys Gly Arg Val Arg
65              70              75              80

Leu Leu Asn Asn Trp Asp Val Cys Ala Asp Met Val Gly Thr Phe Thr
            85              90              95

Asp Thr Glu Asp Pro Ala Lys Phe Lys Met Lys Tyr Trp Gly Val Ala
            100             105             110

Ser Phe Leu Gln Lys Gly Asn Asp Asp His Trp Ile Val Asp Thr Asp
            115             120             125

Tyr Asp Thr Tyr Ala Val Gln Tyr Ser Cys Arg Leu Leu Asn Leu Asp
    130             135             140

Gly Thr Cys Ala Asp Ser Tyr Ser Phe Val Phe Ser Arg Asp Pro Asn
145             150             155             160

Gly Leu Pro Pro Glu Ala Gln Lys Ile Val Arg Gln Arg Gln Glu Glu
            165             170             175

Leu Cys Leu Ala Arg Gln Tyr Arg Leu Ile Val His Asn Gly Tyr Cys
```

-continued

```
                 180              185              190

Asp Gly Arg Ser Glu Arg Asn Leu Leu
        195             200

<210> SEQ ID NO 4
<211> LENGTH: 432
<212> TYPE: PRT
<213> ORGANISM: Homo sapiens

<400> SEQUENCE: 4

Met Glu Arg Arg Arg Ile Thr Ser Ala Ala Arg Arg Ser Tyr Val Ser
1               5                   10                  15

Ser Gly Glu Met Met Val Gly Gly Leu Ala Pro Gly Arg Arg Leu Gly
            20                  25                  30

Pro Gly Thr Arg Leu Ser Leu Ala Arg Met Pro Pro Pro Leu Pro Thr
        35                  40                  45

Arg Val Asp Phe Ser Leu Ala Gly Ala Leu Asn Ala Gly Phe Lys Glu
        50                  55                  60

Thr Arg Ala Ser Glu Arg Ala Glu Met Met Glu Leu Asn Asp Arg Phe
65                  70                  75                  80

Ala Ser Tyr Ile Glu Lys Val Arg Phe Leu Glu Gln Gln Asn Lys Ala
                85                  90                  95

Leu Ala Ala Glu Leu Asn Gln Leu Arg Ala Lys Glu Pro Thr Lys Leu
            100                 105                 110

Ala Asp Val Tyr Gln Ala Glu Leu Arg Glu Leu Arg Leu Arg Leu Asp
        115                 120                 125

Gln Leu Thr Ala Asn Ser Ala Arg Leu Glu Val Glu Arg Asp Asn Leu
        130                 135                 140

Ala Gln Asp Leu Ala Thr Val Arg Gln Lys Leu Gln Asp Glu Thr Asn
145                 150                 155                 160

Leu Arg Leu Glu Ala Glu Asn Asn Leu Ala Ala Tyr Arg Gln Glu Ala
                165                 170                 175

Asp Glu Ala Thr Leu Ala Arg Leu Asp Leu Glu Arg Lys Ile Glu Ser
            180                 185                 190

Leu Glu Glu Glu Ile Arg Phe Leu Arg Lys Ile His Glu Glu Glu Val
            195                 200                 205

Arg Glu Leu Gln Glu Gln Leu Ala Arg Gln Gln Val His Val Glu Leu
        210                 215                 220

Asp Val Ala Lys Pro Asp Leu Thr Ala Ala Leu Lys Glu Ile Arg Thr
225                 230                 235                 240

Gln Tyr Glu Ala Met Ala Ser Ser Asn Met His Glu Ala Glu Glu Trp
                245                 250                 255

Tyr Arg Ser Lys Phe Ala Asp Leu Thr Asp Ala Ala Ala Arg Asn Ala
            260                 265                 270

Glu Leu Leu Arg Gln Ala Lys His Glu Ala Asn Asp Tyr Arg Arg Gln
        275                 280                 285

Leu Gln Ser Leu Thr Cys Asp Leu Glu Ser Leu Arg Gly Thr Asn Glu
        290                 295                 300

Ser Leu Glu Arg Gln Met Arg Glu Gln Glu Glu Arg His Val Arg Glu
305                 310                 315                 320

Ala Ala Ser Tyr Gln Glu Ala Leu Ala Arg Leu Glu Glu Glu Gly Gln
                325                 330                 335

Ser Leu Lys Asp Glu Met Ala Arg His Leu Gln Glu Tyr Gln Asp Leu
            340                 345                 350
```

-continued

```
Leu Asn Val Lys Leu Ala Leu Asp Ile Glu Ile Ala Thr Tyr Arg Lys
        355             360             365

Leu Leu Glu Gly Glu Glu Asn Arg Ile Thr Ile Pro Val Gln Thr Phe
    370             375             380

Ser Asn Leu Gln Ile Arg Glu Thr Ser Leu Asp Thr Lys Ser Val Ser
385             390             395             400

Glu Gly His Leu Lys Arg Asn Ile Val Val Lys Thr Val Glu Met Arg
            405             410             415

Asp Gly Glu Val Ile Lys Glu Ser Lys Gln Glu His Lys Asp Val Met
            420             425             430

<210> SEQ ID NO 5
<211> LENGTH: 76
<212> TYPE: PRT
<213> ORGANISM: Homo sapiens

<400> SEQUENCE: 5

His Pro Leu Gly Ser Pro Gly Ser Ala Ser Asp Leu Glu Thr Ser Gly
1               5               10              15

Leu Gln Glu Gln Arg Asn His Leu Gln Gly Lys Leu Ser Glu Leu Gln
            20              25              30

Val Glu Gln Thr Ser Leu Glu Pro Leu Gln Glu Ser Pro Arg Pro Thr
        35              40              45

Gly Val Trp Lys Ser Arg Glu Val Ala Thr Glu Gly Ile Arg Gly His
    50              55              60

Arg Lys Met Val Leu Tyr Thr Leu Arg Ala Pro Arg
65              70              75
```

METHOD FOR SELECTING A PATIENT FOR A REPERFUSION THERAPY

CROSS-REFERENCE TO RELATED APPLICATIONS

The present application is a 35 U.S.C. § 371 national-phase filing of International Application No. PCT/EP2020/063726, filed on May 15, 2020, which claims the benefit of European Patent Application EP19382384.6, filed on May 16, 2019, both of which applications are incorporated herein by reference in their entirety.

INCORPORATION BY REFERENCE TO SEQUENCE LISTING SUBMITTED

This application contains a sequence listing entitled "108663_00287_SEQLISTING.txt," being submitted herein in ASCII format via EFS-Web, which is a copy of the sequence listing as filed in the PCT/EP2020/063726, which was renamed on Nov. 16, 2021 and is 16,028 bytes in size.

TECHNICAL FIELD

The invention is related to the field of diagnostics or companion diagnostics, in particular to a method of differentiating ischemic stroke from hemorrhagic stroke, and to the selection of proper therapies depending on the type of stroke events.

BACKGROUND ART

Stroke, also called cerebrovascular disease (CVD) remains one of the most important neurological affection. It represents the second leading cause of preventable death worldwide and a major cause of productivity impairment. Two main subtypes of stroke are ischemic stroke (IS) and intracerebral hemorrhage (ICH), also called hemorrhagic stroke. Over 80-85% of all strokes are IS caused by a brain artery occlusion, whereas the remaining 15-20% are ICH that appear due to an arterial rupture. A poorer outcome with a mortality after 30 days from symptoms onset of 37-38% is associated with patients who suffer ICH, in contrast with IS patients who have a 30-days mortality of 8-12%.

An accurate differentiation of both subtypes is critical during acute phase to prescribe the most suitable treatment protocol, which is specific and widely different between IS and ICH. The primary therapy recommended for acute IS includes reperfusion, which is the restoration of blood flow by administration of drugs or by endovascular procedures (Thrombectomy).

Main drugs used are thrombolytic agents such as recombinant tissue plasminogen activator (r-tPA), a serine protease that lysates the clot that occludes the brain artery or Tenecteplase (TNK, a recombinant fibrin-specific plasminogen activator that is derived from native t-PA by modifications at three sites of the protein structure). Thrombolysis has a narrow therapeutic time window of only 4.5 h from symptoms onset, thus a rapid identification of IS might allow an early recanalization leading to a recovery of the tissue from the penumbra and therefore improving the clinical outcome. On the other side, patients with acute ICH are usually managed by reducing blood pressure in order to delay hematoma growth or to avoid edema appearance and rebleedings. Nowadays stroke subtype diagnosis is mainly based on brain imaging data by computerized tomography (CT) or magnetic resonance imaging (MRI). Therefore, patients with suspicion of stroke have to be transferred to hospital to perform such neuroimaging techniques losing a precious time to obtain the CT scan or MRI. Unfortunately, MRI and CT scans are not widely available, especially in undeveloped regions and they cannot be used repeatedly in primary hospital due to the lack of resources. Moreover, some of these techniques may have side effects mainly related with radiation or contrast injections. In addition, MRI and CT may be subject to error or uncertainty if the medical personnel conducting them are not experienced or are inadequately trained.

Among the several documents that describe the use of biomarkers in order to carry out a rapid differentiation of stroke subtypes, international application with publication number WO2016087611 discloses a method for differentiating ischemic stroke from haemorrhagic stroke in a patient and a method for selecting a patient suffering stroke for a therapy with an antithrombotic agent or with an agent capable of reducing blood pressure based on the determination of the level of glial fibrillary acid protein (GFAP) in a sample of said patient in combination with one or more biomarkers.

Another example of a study that analyzes biomarkers that can relate with the acute IS, can be extracted from the document by Reynolds et al., "Early Biomarkers of Stroke", *Clinical Chemistry*-2003, vol.: 49 (10), pp.: 1733-1739. This document shows the results for 5-100B molecules, B-type neurotrophic growth factor, Von Willebrand factor, matrix metalloproteinase-9 (MMP-9), and chemocine ligand 2 (with C-C motif) (CCL-2), also known as chemotactic protein-1 (MCP-1) as possible biomarkers in plasma of patients of stroke. The authors concluded that only the MCP-1 protein had significant value for the diagnosis of acute ischemic stroke, extracting the sample from the cerebrospinal fluid of the patient, although serum concentrations did not differ from those of control patients. Thus, it supposed a low practical approach for the correct identification of the disease.

Biomarkers for the particular diagnosis of cardioembolic stroke have also been disclosed in Montaner et al. "Etiologic Diagnosis of Ischemic Stroke Subtypes With Plasma Biomarkers", Stroke 2008, vol. no. 39, pp.: 2280-2287. Brain natriuretic peptide (BNP) and D-dimer (DD) are there proposed to improve cardioembolic stroke diagnosis in acute phase of stroke.

Precisely due to severity of the disease, the correct diagnosis between stroke subtypes is critical, since administration of a reperfusion therapy in a non-IS patient might be fatal. This subtype diagnosis would be preferably done as soon as possible, in particular once the patient is found in the acute phase at home, at the street or at the general practitioner office. Therefore, a kit or point of care that could be easily implemented in ambulances and that could be further verified at hospital would be a plus.

Other teams are using strategies such as mobile stroke units that are ambulances with an incorporated CT scan in order to be able to do the stroke diagnosis out of the hospital and administer reperfusion therapies as soon as possible to improve the neurological outcome of treated patients. However, this strategy is extremely expensive with enormous costs for those high tech ambulances, requiring specialized personnel.

Recent trials have shown that endovascular treatment for large vessel occlusion (LVO) reduces morbidity and mortality for patients experiencing this form of severe acute ischemic stroke. Nevertheless, a minority of patients experiencing LVO receive endovascular treatment, often due to delays in reaching specialized hospitals where endovascular treatment can be performed (Rai A T et al. (2017). A population-based incidence of acute large vessel occlusions and thrombectomy eligible patients indicates significant potential for growth of endovascular stroke therapy in the USA. *J Neurointerv Surg.* 9:722-6). Patients experiencing acute stroke are often first encountered by Emergency Medical Services (EMS) professionals and early recognition of LVO stroke in the prehospital setting by EMS professionals can improve timely transport to endovascular centers and lead to better patient outcomes (Crowe R P, Myers J B, Fernandez A R, Bourn S, McMullan J T. The Cincinnati Prehospital Stroke Scale Compared to Stroke Severity Tools for Large Vessel Occlusion Stroke Prediction. Prehosp Emerg Care. 2020 Feb. 25:1-9.). Different Scales used for the diagnosis of LVO were compared by Crowe et al. (supra). They showed that in 2,415 patients that experienced an acute ischemic stroke, of 26% of the patients with ischemic stroke were 26% (n=628) were diagnosed with LVO.

A CPSS score of 2 or higher demonstrated a sensitivity of 69% and a specificity of 78% for LVO. A RACE score of 4 or higher demonstrated a sensitivity of 63%, and a specificity of 73%. A LAMS score of 3 or higher demonstrated a sensitivity of 63%, a specificity of 72% and a positive VAN score demonstrated a sensitivity of 86%, and a specificity of 65%. Comparing the area under the ROC curve for each scale revealed no statistically significant differences in discriminative ability for LVO stroke. This make evident the need of reliable markers of LVO.

Moreover, LVO is associated with unfavorable outcomes at 3 and 6 months in patients with acute ischemic stroke (AIS). (Gandhi C D, Al Mufti F, Singh iP, et al. Neuroendovascular management of emergent large vessel occlusion: update on the technical aspects and standards of practice by the Standards and Guidelines Committee of the Society of Neurointerventional Surgery. J Neurointery Surg 2018; 10:315-20). Lakomkin et al found that 16 of the studies included in their systematic review used nine different definitions of LVO (different combinations of locations of arterial occlusions) and this might condition prevalence of LVO as shown by Waqas et al. (see Lakomkin N, Dhamoon M, Carroll K, et al. Prevalence of large vessel occlusion in patients presenting with acute ischemic stroke: a 10-year systematic review of the literature. J Neurointery Surg 2019; 11:241-5; and Waqas M, et al. Effect of definition and methods on estimates of prevalence of large vessel occlusion in acute ischemic stroke: a systematic review and meta-analysis. J Neurointery Surg. 2020 March; 12(3):260-265).

Finally, also noteworthy in the field of stroke diagnosis and treatment is to distinguish the so-called stroke mimics from actual strokes. A stroke mimic is defined as a disease or condition that presents with a stroke-like clinical picture but without neurologic tissue infarction. Several clinical syndromes can present with symptoms or signs that resemble an acute ischemic stroke and, thus, differentiation between a stroke and a stroke mimic is difficult due to the wide variety of overlapping clinical presentations. This is a real challenge for physicians, because of the potential adverse effects of interventional stroke therapies. Few are nowadays the markers in isolated samples of patients that allow distinguishing actual strokes from mimics.

Thus, there is a need in the art of alternative tests using biomarkers to overcome the limitations of the methods disclosed in the art and that can reliably discriminate between stroke subtypes and discarding mimics, in order to decide the best therapeutic approach for the patients and in the shortest time period. Moreover, meanwhile a clear definition of LVO is stablished, there is also an unsatisfied need of reliable markers of LVO, which is a condition that requires a particular treatment (i.e. endovascular treatment or thrombectomy).

SUMMARY OF INVENTION

In a first aspect the invention relates to an in vitro method for selecting a patient suffering stroke for a reperfusion therapy, comprising determining the level of Retinol binding protein-4 (RBP4) and N-terminal fragment of B-type natriuretic peptide (NT-proBNP) in an isolated sample of said patient.

Therefore, this method is encompassed as a companion diagnostic method.

Inventors surprisingly found for the first time that by determining the level of these two proteins in the isolated sample a good classification among IS and ICH could be done.

Thus, another aspect of the invention is an in vitro method for differentiating IS from ICH in a patient, comprising determining the level of RBP4 and NT-proBPN in an isolated sample of said patient.

The levels of NT-proBNP and of RBP4 allow classification of patients within two groups, those that could receive reperfusion therapy, mainly with an antithrombotic agent or by means of thrombectomy, and those that should avoid a reperfusion therapy in order to avoid fatal outcomes. Among the later, ICH patients are then susceptible to be treated with a therapy reducing or optimizing blood pressure.

As depicted in examples below, the levels of NT-proBNP and of RBP4 in combination allow the classification of the patients with a specificity of 100% or near 100%. Therefore, this combination of markers is highly accurate, and it supposes a genuine safe mode of selecting an adequate therapy (i.e. candidate patients for reperfusion therapy). According to the best of inventor's knowledge, this is the first time that markers detectable in isolated samples (i.e. biofluid samples) of patients achieve specificity values of or near 100%. In addition, and highly advantageously, both markers allow discrimination between different stroke types even when measured within 6 hours or less, even 3 hours or less, after symptoms onset. In other words, correct discrimination is possible during critic time (hyperacute phase).

In addition, and as will be illustrated in Examples below, determining these two proteins in the isolated samples allows also to detect those stroke suffering patients with a worse prognosis or outcome in the sense that they have a higher mortality rate. Therefore, those patients would need to be treated as quick as possible to avoid their poor outcome evolution.

Therefore, the invention also relates to a method for the prognosis of a patient suffering stroke, in particular suffering ischemic stroke and thus candidates to reperfusion therapy, which method comprises determining the level of expression of RBP4, optionally in combination of the level of expression of NT-proBNP in an isolated sample of the patient. According to the best of inventor's knowledge, this is the first time this bad outcome association with RBP4 or RBP4 and NT-proBNP has been indicated. In a particular embodiment of the method for the prognosis, levels of both of the proteins are determined in the sample of the patients, which sample is, in another particular embodiment, a biofluid sample; more in particular blood (plasma or serum). In yet another particular embodiment of the method for the prognosis of a patient suffering stroke, the levels of at least RBP4 or the two proteins are compared with a reference value, wherein said reference value is selected from a value or range of values indicating that the subject is suffering ischemic stroke.

In yet another aspect, the invention relates to a kit comprising reagent means for detecting the level of RBP4 and NT-proBNP.

The invention also discloses kits comprising a reagent for detecting the level of a marker selected from GFAP, RBP4, NT-proBNP or a combination thereof.

In yet another aspect, the invention aims also the use of means for detecting the presence of any of RBP4, NT-proBNP in a test sample, said means being selected from the group consisting of immunoassays, protein migration, chromatography, mass spectrometry, turbidimetry, nephelometry and polymerase chain reaction (PCR), for carrying out method for selecting a patient suffering stroke for a reperfusion therapy, as defined in the first aspect; or for differentiating ischemic stroke from hemorrhagic stroke in a patient.

DETAILED DESCRIPTION OF THE INVENTION

Figure 1:
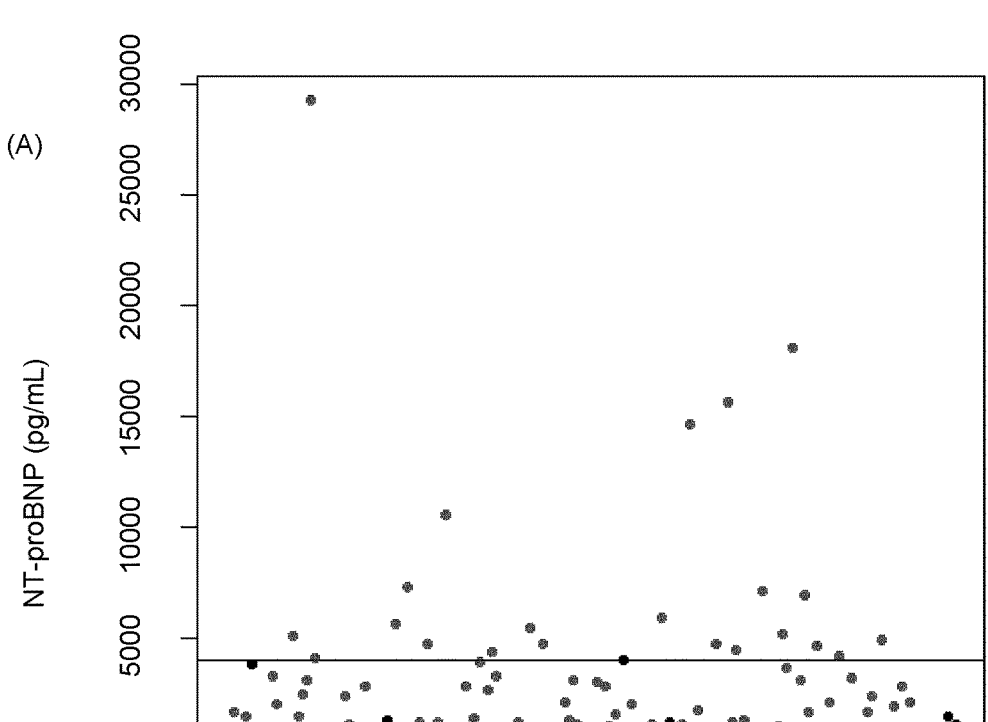
FIG. 1 shows in (A) the cut-off (horizontal black line) level for NT-proBNP (Y-axis in pg/mL) for a 100% specificity of the two stroke subtypes; and in (B) the cut-off (horizontal black line) level for RBP4 (Y-axis in pg/mL). In panel C, log 10(NT-proBNP) and RBP4 levels were simultaneously plotted with the corresponding previously determined cut-offs for each protein. 100% specificity IS means that all patients with values in that space of the graphic (figure) were all ischemic stroke patients.
Figure 1:
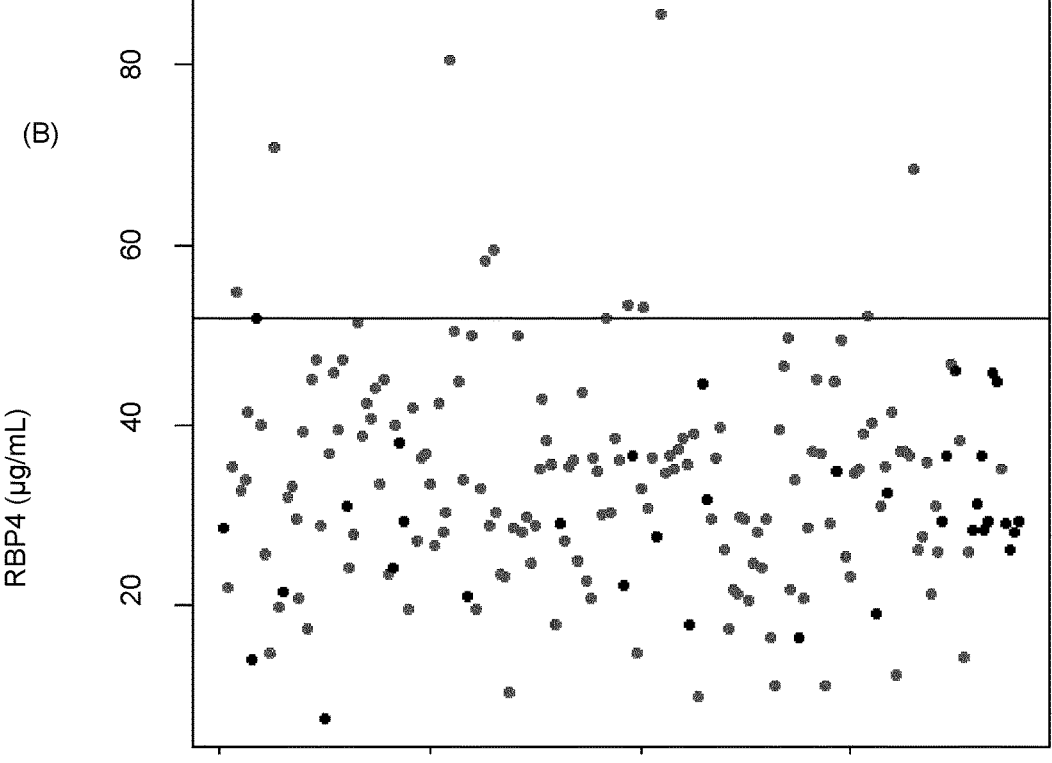

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

The term "patient" (or subject), as used herein, refers to any subject which show one or more signs or symptoms typically associated with stroke such as sudden-onset face weakness, arm drift, abnormal speech as well as combination thereof such as the FAST (face, arm, speech, and time), hemiplegia and muscle weakness of the face, numbness, reduction in sensory or vibratory sensation, initial flaccidity (hypotonicity), replaced by spasticity (hypertonicity), hyperreflexia, obligatory synergies and, in particular, when they appear in one side of the body (unilateral), altered smell, taste, hearing, or vision (total or partial), drooping of eyelid (ptosis) and weakness of ocular muscles, decreased reflexes (e.g. gag, swallow, pupil reactivity to light), decreased sensation and muscle weakness of the face, balance problems and nystagmus, altered breathing and heart rate, weakness in sternocleidomastoid muscle with inability to turn head to one side, weakness in tongue (inability to protrude and/or move from side to side), aphasia, dysarthria, apraxia, visual field defect, memory deficits, hemineglect, disorganized thinking, confusion, hypersexual gestures, lack of insight of his or her, usually stroke-related, disability, altered walking gait, altered movement coordination, vertigo, headache and or disequilibrium. The term "patient", as used herein, refers also to all animals classified as mammals and includes, but is not restricted to, domestic and farm animals, primates and humans, e.g., human beings, non-human primates, cows, horses, pigs, sheep, goats, dogs, cats, or rodents. Preferably, the patient is a male or female human of any age or race. Preferably the patient suffers stroke.

The term "selecting a patient for a therapy", as used herein, relates to the identification of a patient for a therapy designed to cure a disease or palliate the symptoms associated with one or more diseases or conditions. In the particular case of a stroke therapy, it is understood any therapy which abolishes, retards or reduces the symptoms associated with stroke and, more in particular, with ischemic stroke or alternatively with hemorrhagic stroke.

The term "reperfusion therapy" relates to a medical treatment to restore blood flow, either through or around, blocked arteries. Reperfusion therapy includes drugs and endovascular procedures. The drugs are thrombolytics (antithrombotic agents) and fibrinolytics used in a process called thrombolysis. Interventions performed may be minimally-invasive endovascular procedures for removing the thrombus (thrombectomy), with the possible use of one or more stent-retrievers, aspiration techniques or alternatives devices that combine both stent-retrievers and aspiration. Other surgeries performed are the more invasive bypass surgeries that graft arteries around blockages. "Mechanical thrombectomy", or simply thrombectomy, is the interventional procedure of removing a blood clot (thrombus) from a blood vessel. It is commonly performed in the coronary arteries (interventional cardiology), peripheral arteries (interventional radiology) and cerebral arteries (interventional neuroradiology).

The selection of a patient, although preferred to be, need not be adequate for 100% of the subjects selected according to this first method of the invention. The term, however, requires that a statistically significant portion of subjects be correctly selected. Whether the selection of a patient in a population of subjects is statistically significant can be determined by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%>, at least 70%>, at least 80%>, at least 90%>, or at least 95%. The p-values are, preferably, 0.01, 0.05, 0.005, 0.001 or lower.

The term "ischemic stroke" (abbreviated IS) refers to the physical blockage of blood flow to an area of the brain, causing brain cells in the area to die. Ischemic strokes can further be divided into thrombotic and embolic strokes. Thrombotic strokes occur when a brain artery is blocked by a blood clot formed in the brain. Embolic strokes are caused by a thrombus, which is formed in a peripheral artery or in the heart that travels to the brain where it produces ischemia. Another type of ischemic strokes are lacunar strokes due to the occlusion of a small cerebral artery.

The term "hemorrhagic stroke" (abbreviated ICH if intracerebral haemorrhage), as used herein refers to a bleeding into the brain tissue due to a blood vessel burst.

Inventors of present invention have identified RBP4 and BNP as new plasma biomarkers for accurately selecting a patient suffering from stroke for a reperfusion therapy. Thus, the markers can differentially diagnose acute IS from ICH. By means of several data analysis approaches with these two markers, 100% of specificity was achieved with a sensitivity of 20%-30%. In addition, if a third marker was added, in particular the levels of GFAP, specificity was maintained while sensitivity increased at 60%.

Thus, in a particular embodiment of the first aspect of selecting a patient suffering stroke for a reperfusion therapy, the method further comprises determining the level of GFAP in the isolated sample of said patient.

Although an increase of sensitivity is desirable, inventors have also developed a simplified kit comprising only means for detecting the levels of RBP4 and NT-proBNP. With this simplified kit, that can be used in ambulance when a stroke patient is being attended, an accurate discrimination between IS and ICH can be performed. This allows administration of the reperfusion therapy, if proper, as soon as possible (i.e antithrombotic agent at ambulance); and to avoid a bad outcome at least in IS because the patients are treated soon. In addition, in ICH a worsening of the symptoms is avoided if blood pressure might be optimized.

In yet a more particular embodiment of the first aspect, the method comprises the step of comparing said levels with a corresponding reference value or reference interval for each protein, said reference value or interval selected from a value or interval of values from a subject suffering from ischemic stroke, and wherein the subject is classified as a candidate for a reperfusion therapy when at least the level of RBP4 and of NT-proBNP are both within the value or interval of values from a subject suffering from IS.

In a more particular embodiment, the reference value or interval is selected from a value or interval of values from a subject suffering from IS or from a subject suffering from ICH, the subject is classified as a candidate for a reperfusion therapy when at least the level of RBP4 and of NT-proBNP are both within the value or interval of values from a subject suffering from IS. With the levels of both within the value or interval of values from a subject suffering from IS a meaningful clinical sensitivity (around 21%) is achieved for a specificity over 98%, in particular of the 100%.

In another particular embodiment of the first aspect, the method comprises the step of comparing the levels of RBP4, NT-proBNP and optionally of GFAP if determined, with a corresponding reference value or reference interval for each protein, said reference value or interval selected from a value or interval of values from a subject suffering from ischemic stroke, and wherein the subject is classified:

as a candidate for a reperfusion therapy, and as having a prognosis defined by a dependency degree greater than 2 according to modified ranking score (mRS), and determined within 1-5 months after stroke onset and/or as having a prognosis defined by a three-month after onset mortality rate comprised from 20% to 30%.

when at least the level of RBP4 and of NT-proBNP are both within the value or interval of values from a subject suffering from ischemic stroke.

In another more particular embodiment, the method comprises the step of comparing the levels of RBP4, NT-proBNP and of GFAP, and wherein if the subject is classified as candidate for a reperfusion therapy it is also classified as having a prognosis defined by a dependency degree greater than 2 according to modified ranking score (mRS), and determined within 1-5 months after stroke onset; and/or as having a prognosis defined by a three-month after onset mortality rate comprised from 20% to 30%.

The prognosis can also be defined as a dependency degree greater than 2 according to modified ranking score (mRS), and determined at least three months after stroke onset. In a particular embodiment the three-month after onset mortality rate is of at least 23%. In another particular embodiment is of 25%.

In certain embodiments with only one of the levels of RBP4 and of NT-proBNP are within the value or interval of values from a subject suffering from IS, the subject is also classified as candidate for reperfusion.

In another particular embodiment of the first aspect, the in vitro method further comprises the step of comparing the levels of RBP4, NT-proBNP and if determined of GFAP, with a corresponding reference cut-off value for each protein, wherein:

if only the levels of RBP4 and NT-proBNP are determined, a level of RBP4 and of NT-proBNP simultaneously equal or higher than corresponding reference cut-off values for each of the proteins, $\text{Ref1}_{RBP4}$ and $\text{Ref1}_{NT-proBNP}$, said cut-off values discriminating between ischemic stroke patients and intracerebral haemorrhage patients is indicative that the patient is a candidate for a reperfusion therapy; or if the levels of RBP4, NT-proBNP and additional GFAP are determined, the patient is selected as a candidate for a reperfusion therapy if in a first step the level of GFAP is equal or lower than a reference cut-off value $\text{Ref}_{GFAP}$; and in a second step the level of RBP4 and of NT-proBNP are simultaneously equal or higher than corresponding references cut-off values $\text{Ref2}_{RBP4}$ and $\text{Ref2}_{NT-proBNP}$, said cut-off values discriminating between ischemic stroke patients and intracerebral haemorrhage patients.

Indeed, the different alternative embodiments of the method of the first aspect when including the option of comparing tested levels with respective cut-off values or reference intervals are selected considering particular values of desired sensitivities and specificities. Thus, if a 100% specificity (correct classification between two conditions) is desired, sensitivity (detection of one condition among a cohort of subjects with different conditions) can be lowered. On the other hand, lowering the specificity (i.e. around 94% or 98%) allows increasing sensitivity of a method. Therefore, reference values can be varied depending on the desired specificity and/or sensitivity desired.

In a more particular embodiment of this method including comparison with cut-off values of the two or the three protein levels, if the subject is classified as candidate for a reperfusion therapy, it is also classified as having a prognosis defined by a dependency degree greater than 2 according to modified ranking score (mRS), and determined within 1-5 months after stroke onset; and/or as having a prognosis defined by a three-month after onset mortality rate comprised from 20% to 30%.

Also encompassed herewith is, as another particular embodiment of the method of the first aspect for selecting a patient suffering stroke for a reperfusion therapy, that it further includes a step of treating the patient with said reperfusion therapy if at least the level of RBP4 and of NT-proBNP are both within the value or interval of values from a subject suffering from IS; or in the alternative, if corresponding reference cut-off values of RBP4 and of NT-proBNP, an optionally of GFAP, classify the patient as candidate for reperfusion therapy.

As above indicated, there are several therapy protocols for the promotion of reperfusion. In a particular embodiment of the first aspect of the invention, the reperfusion therapy is selected from the group consisting of a therapy with an antithrombotic agent, thrombectomy and a combination thereof.

In a more particular embodiment, the antithrombotic agent is a thrombolytic agent. In yet a more particular embodiment, the thrombolytic agent is a plasminogen activator. More in particular, the plasminogen activator is tissue plasminogen activator.

The term "antithrombotic agent", as used herein, refers to a drug that is able to reduce clot formation. Suitable antithrombotic agents for use in the present invention include, without limitation, thrombolytic agents, antiplatelet agents and anticoagulant compounds.

The term "thrombolytic agent" as used herein refers to a drug that is able to dissolve a clot. All thrombolytic agents are serine proteases and convert plasminogen to plasmin which breaks down the fibrinogen and fibrin and dissolves the clot. Currently available thrombolyic agents include reteplase (r-PA or Retavase), alteplase (t-PA or Activase), urokinase (Abbokinase), prourokinase, anisoylated purified streptokinase activator complex (APSAC), staphylokinase (Sak), tenecteplase (TNK-tPA), atenecteplase (TNKasa), anistreplase (Eminase), streptoquinase (Kabikinase, Streptase) or uroquinase (Abokinase). Tenecteplase (TNK-tPA) is used in a particular embodiment, since it can be administered as a fast single bolus and can be used at ambulance level. TNK is effective after 1 minute post-administration (post-injection). Providers for TNK are Boehringer Ingelheim (European Union) and Genentech Inc (USA).

The term anticoagulant compounds, as used herein, refers to compounds that prevent coagulation and include, without limitation, vitamin K antagonists (warfarin, acenocumarol, fenprocoumon and fenidione), heparin and heparin derivatives such as low molecular weight heparins, factor Xa inhibitors such as synthetic pentasaccharides, direct thrombin inhibitors (argatroban, lepirudin, bivalirudin and ximelagatran) and antiplatelet compounds that act by inhibition of platelet aggregation and, therefore, thrombus formation and include, without limitation, cyclooxygenase inhibitors (aspirin), adenosine diphosphate receptor inhibitors (clopidogrel and ticlopidine), phosphodiesterase inhibitors (cilostazol), glycoprotein IIB/IIIA inhibitors (Abciximab, Eptifibatide, Tirofiban and Defibrotide) and adenosine uptake inhibitors (dipiridamol). In a preferred embodiment, the antithrombotic agent is a thrombolytic agent. In a more preferred embodiment, the thrombolytic agent is a plaminogen activator. In a yet more preferred embodiment, the plasminogen activator is tPA (tissue plasminogen activator).

The term "tissue plasminogen activator (t-PA)" as used herein refers to a serine protease found on endothelial cells that catalyzes the conversion of plasminogen to plasmin. The complete protein sequence for human t-PA has the UniProt KB accession number P00750 (Jul. 11, 2012), SEQ ID NO: 1. tPA may be manufactured using recombinant biotechnology techniques, tPA created this way may be referred to as recombinant tissue plasminogen activator (rtPA). Recombinant tissue plasminogen activators (r-tPAs) include the thrombolytic agents alteplase, reteplase, and tenecteplase (TNKase, also termed TNK-tPA, SEQ ID NO: 2). In human t-PA, the amino acids at position 296-299 are lysine, histidine, and two arginines. In TNK-tPA, these amino acids have been replaced by four alanines. This mutation is responsible for increased resistance to plasminogen activator inhibitor 1 (PAI-1).

Doses of t-PA should be given within the first 3 hours of the onset of symptoms or up to 4.5 hours from symptom onset. Recommended total dose: 0.9 mg/kg (maximum dose should not exceed 90 mg) infused over 60 minutes. Load with 0.09 mg/kg (10% of the 0.9 mg/kg dose) as an intravenous bolus over 1 minute, followed by 0.81 mg/kg (90% of the 0.9 mg/kg dose) as a continuous infusion over 60 minutes. Heparin should not be started for 24 hours or more after starting alteplase for stroke. Said t-PA is given intravenously and in some cases may be given directly into an artery and should be given right away after the first symptoms of stroke start. Said doses and administration routes apply to any of the embodiments of the first aspect. Also, in particular in embodiments including step of treating the patient.

Single dose of TNK-tPA should be given as soon as possible after determining that the subject suffering from stroke is a candidate to reperfusion therapy, and within the first 3 hours of the onset of symptoms or up to 4.5 hours from symptom onset, preferably within the first hour after stroke onset.

As indicated above, the use of TNK-tPA is particularly useful, since due to the particular formulation as fast single application bolus, it can be administered at any point of care, even at ambulance level, being effective about one minute post-administration.

Those patients suffering stroke not selected for a reperfusion therapy, are in a particular embodiment, selected for a therapy reducing blood pressure. In particular, said therapy is performed with an agent capable of reducing blood pressure.

"Blood pressure" is herein to be understood as to refer to the blood pressure at the site of central arteries, such as the aorta and carotid artery. Central blood pressure can suitably be measured non-invasively (as set out below) at the carotids or radialis by applanation tonometry. "Blood pressure" as used herein thus encompasses aortic blood pressure.

"Agent capable of reducing blood pressure", as used in the present invention, relates to any drug which lower blood pressure by different means. Among the most widely agents are the thiazide diuretics [such as furosemide, nitroprusside, hydralazine]; the ACE inhibitors, the calcium channel blockers (such as nicardipine or nimodipine); the adrenergic receptor antagonist (such as alpha-adrenergic antagonist, urapidil), or combined alpha- and beta-blocker (labetalol and nitroglycerin); and the angiotensin II receptor antagonists (ARBs). Illustrative, non-limitative example of agents capable of lowering or reducing blood pressure are alphamethyl dopa (Aldomet), 11,17alpha-d.imethoxy-18β-[(3,4,5-trimethoxy-benzoyl)oxyl)]-3p,2a-yohimban-16β-carboxylic acid methyl ester (Reserpine) or 2-(2,6-dichlorophenylamino) 2-imidazoline hydrochloride (Clonidine hydrochloride), lergotrile or viz. 2-chloro-6-methylergoline-8β-acetonitrile as disclosed in EP0005074. Reference values that will be used to decrease blood pressure in ischemic stroke, ischemic stroke treated with thrombolytics or hemorrhagic stroke, will be those recommended by clinical practice guidelines as these values could be updated. Nowadays, treatment modalities for blood pressure lowering are aimed to be reduced if systolic blood pressure to among 220-120 mm Hg was achieved in ischemic patients and if it achieved to among 180-100 mm Hg in haemorrhagic patients. In a preferred embodiment, the blood pressure may be reduced by intravenous administration of an agent capable of reducing blood pressure and co-administration of oral antihypertensive agent(s). Reference values that will be used to decrease blood pressure in ischemic stroke, ischemic stroke treated with thrombolytics or hemorrhagic stroke, will be those recommended by clinical practice guidelines as these values could be updated.

Any method suitable for measure arterial pressure can be used for determining if an agent is capable of reducing blood pressure, wherein a reduction in arterial pressure is detected after administration of the agent. Illustrative, non-limitative examples of methods for measurement arterial pressure are non-invasive techniques, such as by way of illustrative non-limitative example palpitation, auscultatory, oscillometric and continuous noninvasive arterial pressure (CNAP).

The term "reference value", as used herein, relates to a predetermined criteria used as a reference for evaluating the values or data obtained from the samples collected from a subject. The reference value or reference level can be an absolute value; a relative value; a value that has an upper or a lower limit; a range of values; an average value; a median value, a mean value, or a value as compared to a particular control or baseline value. A reference value can be based on an individual sample value, such as for example, a value obtained from a sample from the subject being tested, but at an earlier point in time. The reference value can be based on a large number of samples, such as from population of subjects of the chronological age matched group, or based on a pool of samples including or excluding the sample to be tested. Reference values have been determined for the biomarkers of the invention. The reference value for each of RBP4, NT-proBNP and GFAP may be from a lower and an upper value as will be disclosed in view of examples below. Range of values of each biomarker (protein levels) and particular combinations of the values of the different biomarkers provide for correct classification of subjects with high sensitivity and specificity.

The levels of a bio marker (in this invention any of NT-proBNP, RBP4 or GFAP) are considered to be higher than its reference value when it is at least 1.5%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%: at least 85%, at least 90%, at least 95%, at least 100%, at least 110%, at least 120%, at least 130%, at least 140%, at least 150% or more higher than the reference value.

Likewise, in the context of the present invention, the level of a biomarker is reduced when the level of said biomarker in a sample is lower than a reference value. The levels of a biomarker are considered to be lower than its reference value when it is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%: at least 85%, at least 90%, at least 95%, at least 100%, at least 110%, at least 120%, at least 130%, at least 140%, at least 150% or more lower than the reference value.

In a particular embodiment of the first aspect, when only the levels of RBP4 and NT-proBNP are determined in a biofluid sample and compared with corresponding reference cut-off values (herewith termed $\text{Ref1}_{RBP4}$ and $\text{Ref1}_{NT-proBNP}$), these reference cut-off values are for RBP4 52 µg/ml, for NT-proBNP 4062 pg/ml. These particular reference cut-off values are, in a particular embodiment, for isolated plasma samples and when assayed with an enzyme immunosorbent assay (ELISA)

In another particular embodiment of the first aspect, when the levels of RBP4, NT-proBNP and GFAP are determined and compared with corresponding reference cut-off values (herewith termed $\text{Ref2}_{RBP4}$, $\text{Ref2}_{NT-proBNP}$ and $\text{Ref}_{GFAP}$) these reference cut-off values are: for RBP4 38 µg/ml, for BNP 1305 pg/ml, and for GFAP 0.325 ng/ml. These particular reference cut-off values are, in a more particular embodiment, for isolated plasma samples and when GFAP was assayed, the levels of this marker is determined with a more sensitive (picomolar level) single molecular assay (SIMOA) and the others with an ELISA assay. With these cut-off levels, a particular method is carried out in two separate steps or conditions. In a first step the level of GFAP is determined and if it is equal or lower than the reference cut-off value $\text{Ref}_{GFAP}$, patients are considered as suffering from ischemic stroke and candidates for reperfusion if further in a second step the level of RBP4 and of NT-proBNP are simultaneously equal or higher than corresponding references cut-off values $\text{Ref2}_{RBP4}$ and $\text{Ref2}_{NT-proBNP}$.

As will be illustrated by means of the examples, ICH patients had higher GFAP levels and lower RBP4 and NT-proBNP than IS. The combination of RBP4>52 µg/mL and GFAP>0.18 ng/mL resulted in an accurate diagnosis of 6.5% of IS and 34.3% of ICH. The addition of the NT-proBNP kept 100% specificity and improved sensitivity for IS up to 20% (31/155) by using RBP4>52 µg/mL and the BNP cut-off>4060 pg/mL.

As above indicated, it is widely known that reference values can vary depending on exclusion criteria decisions of clinical protocols. In addition, depending on the variables that are considered to make a diagnosis, these values can also be modulated always in order to increase sensitivity while maintaining specificity, which specificity is really critical in stroke.

Moreover, proper classification of patients depending on detected levels of the proteins can be done using computational methods, by which of them the determined values of proteins are computed in a formula that gives a predictive factor, said predictive factor calculated based on the expression levels of the proteins, said expression levels being corrected by a particular coefficient. Other computation methods (such as one of the exemplified herewith and called support vector machine method), allow disclosing a function that properly classify the patients considering the levels of all determined proteins.

All these reference values indicated in the particular embodiments are the ones determined in isolated plasma samples of subjects suffering from stroke. The skilled man will know how to find the corresponding ones in serum and other bio fluids.

The term "sample" as used herein, relates to any sample which can be obtained from the patient. The present method can be applied to any type of biological sample from a patient, such as a biopsy sample, tissue, cell or biofluid (plasma, serum, saliva, semen, sputum, cerebral spinal fluid (CSF), tears, mucus, sweat, milk, brain extracts and the like.

Therefore, in another particular embodiment, optionally in combination with any embodiment above or below, the isolated sample of the subject (i.e. patient suffering stroke) is a bio fluid. Illustrative non limitative bio fluids are blood, plasma, serum, saliva, urine or cerebrospinal fluid. In a more preferred embodiment, the biofluid is plasma or serum.

In a preferred embodiment of the methods of the invention, the sample is obtained at baseline.

Different samples could be used for determining the level of different markers. Thus, it is not necessary that the levels of all the markers according to the methods of the invention are measured in the same type of sample. Thus, in another preferred embodiment, the levels of RBP4, NT-proBNP and GFAP are measured in serum. In another preferred the level of they are measured in plasma.

"Baseline", as used in the present invention, is considered any time from onset of symptoms until the patient is explored for the first time. This is usually within the first hours after stroke, and it is usually the first attention in the ambulance or in the hospital. In a preferred embodiment, the baseline is within the first 4.5 hours from symptom onset, or less than 6 hours after stroke or in another preferred embodiment less than 24 hours symptoms onset.

In another particular embodiment of this aspect, the step of determining the level of RBP4 and of NT-proBNP, and if determined of GFAP, is carried out within the two first hours after the stroke onset. As will be depicted in examples below, the sooner the determination of the markers in the isolated sample is done, the better the accuracy and sensitivity of the method. In another particular embodiment of this aspect, the step of determining the level of RBP4 and of NT-proBNP, and if determined of GFAP, is carried out within the first hour after the stroke onset.

In another embodiment of the first aspect of the method for selecting a patient suffering stroke for a reperfusion therapy, it further comprises determining one or more clinical parameters. Thus, the method of the invention comprises determining the levels of RBP4 and BNP and one or more clinical parameters.

The term "clinical parameters" or clinical data, as used herein, refers to person demographics (age or date of birth, race and/or ethnicity), patient clinical symptoms or signs related to stroke related diseases/conditions. The term also includes laboratory parameters, such as the determination of d-dimer or of glycemia.

In a particular embodiment, the clinical parameter is hypertension and wherein if the patient has hypertension is indicative that the patient suffers ischemic stroke or that the patient is a candidate for a reperfusion therapy.

In another particular embodiment of the first aspect, the in vitro method further comprises determining a clinical parameters selected from the group consisting of blood pressure, including systolic blood pressure and/or diastolic blood pressure, glycemia, age, scores from systematic assessment tool stroke-related neurologic deficit, such as NIHSS score, gender, and combinations thereof. The values of all these parameters are, in a particular embodiment, used in combination with the levels of RBP4, NT-proBNP and optionally of GFAP in adequate algorithms for correctly classifying the patient as candidate to reperfusion therapy. For example, blood pressure within a certain interval in combination with certain levels of the two or three proteins are used in a decision protocol for the correct classification. The values are, in another more particular embodiment, introduced in formulas of regression models to give a score or final value allowing such classification.

For "hypertension", sometimes called arterial hypertension, is to be understood a chronic medical condition in which the blood pressure in the arteries is elevated. Normal blood pressure at rest is within the range of 100-140 mmHg systolic (top reading) and 60-90 mmHg diastolic (bottom reading). High blood pressure is said to be present if it is persistently at or above 140/90 mmHg. As above indicated, reference values that will be used to decrease blood pressure in ischemic stroke, ischemic stroke treated with thrombolytics or haemorrhagic stroke, will be those recommended by clinical practice guidelines as these values could be updated, being nowadays accepted as suitable treatment modalities for blood pressure lowering when systolic blood pressure amounts to among 220-120 mm Hg in ischemic patients and amounts to among 180-100 mm Hg in haemorrhagic patients.

The term "systematic assessment tool stroke-related neurologic deficit" relates to tools designed to measure and scale the neurological deficits most often seen with stroke. Several aspects or parameters are assessed, such as the level of consciousness, visual fields, facial weakness, motor performance of extremities, gaze, sensory deficits, coordination (ataxia), language (aphasia), speech (dysarthria), etc. For all of them a value is given, being 0 if normal. So, in most of these tools the higher the score, the worse the neurological deficit. The skilled man will know of the existence of different tools for this purpose, as the National Institutes of Health Stroke Scale (NIHSS) score, the Rapid Arteria occlusion evaluation scale for stroke (RACE), the Cincinnati Prehospital Stroke Scale Compared to Stroke Severity Tools for Large Vessel Occlusion Stroke Prediction (Cincinnati-score), Los Angeles Motor Scale (LAMS), or the modified Rankin Scale or Score (mRS). All these scales are designed to provide a rapid and standardized assessment of the neurological function in the early periods after stroke. The modified Rankin Scale or Score (mRS) is also a scale for evaluating the degree of disability after the stroke onset. It is mostly applied at discharge and 3 months after onset.

In another preferred embodiment the clinical parameter is selected from age, NIHSS score, gender, systolic blood pressure and combinations thereof. The term "NIHSS score", as used in the present invention refers to The National Institutes of Health Stroke Scale (NIHSS) score, a systematic assessment tool that provides a quantitative measure of stroke-related neurologic deficit (Adams H P Jr Neurology. 1999 Jul. 13; 53(1): 126-31). The NIHSS was originally designed as a research tool to measure baseline data on patients in acute stroke clinical trials. Now, the scale is also widely used as a clinical assessment tool to evaluate acuity of stroke patients, determine appropriate treatment, and predict patient outcome. The NIHSS is a 15-item neurologic examination stroke scale used to evaluate the effect of acute cerebral infarction on the levels of consciousness, language, neglect, visual-field loss, extraocular movement, motor strength, ataxia, dysarthria, and sensory loss. A trained observer rates the patient's ability to answer questions and perform activities. Ratings for each item are scored with 3 to 5 grades with 0 as normal, and there is an allowance for untestable items. The level of stroke severity as measured by the NIH stroke scale scoring system: 0=no stroke, 1-4=minor stroke, 5-15=moderate stroke, 15-20=moderate/severe stroke, 21-42=severe stroke. In the present invention the term "higher score" refers to a score from 5 to 42 in the NIH stroke scale scoring system.

Also variations of the NIHSS such as Rapid Arteria occlusion evaluation scale for stroke (RACE) or other scores used to identify ischemic strokes with large vessel occlusion may be used.

Yet in another particular embodiment of the first aspect, optionally in combination with any of the embodiments above or below, if the subject is classified as candidate for a reperfusion therapy, it is also diagnosed of suffering from large vessel occlusion.

As a second aspect the invention relates to an in vitro method for differentiating IS from ICH in a patient, comprising determining the level of RBP4 and NT-proBPN in an isolated sample of said patient.

In a particular embodiment of the second aspect, the method comprises determining the level of GFAP.

In another more particular embodiment of the second aspect, it further comprises the step of comparing the levels of RBP4, NT-proBNP and if determined of GFAP, with a corresponding reference value, wherein:

if only the levels of RBP4 and BNP are determined, a level of RBP4 and of BNP simultaneously higher than corresponding reference values $Ref1_{RBP4}$ and $Ref1_{NT\text{-}proBNP}$ is indicative that the patient is an IS patient; or if the levels of RBP4, BNP and GFAP are determined, a level of RBP4 and of BNP simultaneously higher than corresponding references values $Ref2_{RBP4}$ and $Ref2_{NT\text{-}proBNP}$, and a level of GFAP lower than a reference value $Ref_{GFAP}$ is indicative that the patient is an IS patient.

In another particular embodiment of the second aspect, if the subject is classified as an ischemic stroke when determining the levels of RBP4 and BNP and optionally of GFAP, it is also classified as having a prognosis defined by a dependency degree greater than 2 according to modified ranking score (mRS), and determined within 1-5 months after stroke onset; and/or as having a prognosis defined by a three-month after onset mortality rate comprised from 20% to 30%.

In another particular embodiment of the second aspect, it further comprises the step of selecting a therapy, in particular reperfusion therapy, as indicated in the first aspect and its particular embodiments.

Thus, after differential diagnosis is accomplished, in another particular embodiment of the second aspect it further comprises a step of recommending a reperfusion therapy to a patient diagnosed of IS and/or treating said patient diagnosed of IS with a reperfusion therapy, mainly with an antithrombotic agent or by means of thrombectomy. On the alternative, those patients diagnosed of ICH that should avoid a reperfusion therapy in order to avoid fatal outcomes are, in another particular embodiment, recommended for or treated with a therapy reducing or optimizing blood pressure.

This particular embodiment could be drafted as a method of treating a patient suffering stroke, said method comprising carrying out the in vitro method for differentiating IS from ICH in a patient according to the second aspect and treating a patient diagnosed of IS with a reperfusion therapy, mainly with an antithrombotic agent or by means of thrombectomy; or treating a patients diagnosed of ICH with a therapy reducing or optimizing blood pressure. Advantageously, with this method patient is treated or recommended to be treated within first hours of the onset of symptoms and with the most appropriate therapy regimen.

All particular embodiments previously disclosed for the first aspect do also apply to this second aspect. In particular, those preferred reference values, the kind of isolated sample and the option of further determining one or more clinical parameters. Thus, in another particular embodiment of the second aspect, the in vitro method further comprises determining a clinical parameters selected from the group consisting of blood pressure, including systolic blood pressure and/or diastolic blood pressure, glycemia, age, scores from systematic assessment tool stroke-related neurologic deficit, such as NIHSS score, gender, and combinations thereof. As before, the values of all these parameters are, in a particular embodiment, used in combination with the levels of RBP4, NT-proBNP and optionally of GFAP in adequate algorithms for correctly classifying the patient as candidate to reperfusion therapy. For example, blood pressure within a certain interval in combination with certain levels of the two or three proteins are used in a decision protocol for the correct classification. The values are, in another more particular embodiment, introduced in formulas of regression models to give a score or final value allowing such classification.

Also, in another particular embodiment of the second aspect, the determining the level of RBP4 and of NT-proBNP, and if determined of GFAP, is carried out within the two first hours after the stroke onset. More in particular within the first hour. This implies the advantage of increasing sensitivity of the method as indicated for the first aspect.

Yet, in another particular embodiment of this second aspect, optionally in combination with any of the embodiments above or below, if the subject is classified an ischemic stroke, it is also diagnosed of suffering from large vessel occlusion.

Invention also generically encompasses a method of detecting, in an isolated sample of a subject suffering from stroke, the level of RBP4 and NT-proBPN, and optionally in combination with the level of GFAP, the method comprising:

(a) obtaining a sample from the subject; and (b) detecting whether one or more of the proteins is present in the isolated sample by: (i) contacting said sample with means capable of binding the corresponding expressed proteins and detecting said binding; or (ii) contacting said sample with means capable of binding corresponding RNA going to be translated to the one or more of the corresponding proteins and detecting said binding.

The term "differentiating", as used herein for the second aspect, relates to the determination of a different condition. As will be understood by those skilled in the art, differentiation, although preferred to be, need not be correct for 100% of the subjects to be diagnosed or evaluated. The term, however, requires that a statistically significant portion of subjects can be identified as having an increased probability of having one of the two types of stroke. Whether a subject is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at least 90%, or at least 95%. The p-values are, preferably, 0.05, 0.01, 0.005 or lower.

Since the biomarkers identified in the present invention allow differentiating IS from ICH in a patient and considering that different therapies are applied to these two types of patients (antithrombotic agents in patients suffering ischemic stroke and an agent capable of reducing blood pressure in patients suffering haemorrhagic stroke) (see Tsivgoulis G. et al, Neurology. 2014 Sep. 19), the invention also provides the above-mentioned first method for the selection of a therapy for a patient having suffered stroke. Thus, both aspects are intimately and conceptually related.

When in present invention RBP4 is referred, it relates to refers to retinol binding protein 4, plasma that belongs to the lipocalin family and is the specific carrier for retinol in the blood. The complete sequence for human retinol binding protein 4 has the UniProtKB accession number P02753 (Aug. 8, 2013), SEQ ID NO: 3.

The term "GFAP" as used herein refers to glial fibrillary acidic protein, an intermediate filament protein that is expressed by numerous cell types of the central nervous system. The complete human sequence for glial fibrillary acidic protein has the UniProtKB accession number P14136 (Aug. 8, 2013), SEQ ID NO: 4.

The N-terminal fragment of B-type natriuretic peptide (NT-proBNP) (SEQ ID NO: 5) is the 76-amino acid N-terminal fragment of the B-type natriuretic peptide prohormone. Cleaving of pro-BNP yields the NT-proBNP fragment and the active B-type natriuretic peptide (BNP). BNP is a hormone secreted by cardiomyocytes in the heart ventricles in response to stretching caused by increased ventricular blood volume. The complete human sequence BNPhas the UniProt KB accession number P16860 (Aug. 1, 1990—version 1 of the sequence, and database release 187 of May 8, 2019).

All these proteins do have homologues in other mammal species (cats, dogs, mouse, rats, etc.). The skilled man can retrieved the corresponding complete sequences in public databases.

As the person skilled in the art understands, the expression levels of NT-proBNP, RBP4 and/or GFAP can be determined by measuring the levels of mRNA encoded by the corresponding genes or by measuring the levels of proteins encoded by said genes, and the levels of variants thereof.

By way of a non-limiting illustration, the expression levels are determined by means of the quantification of the levels of mRNA encoded by said genes. The latter can be quantified by means of using conventional methods, for example, methods comprising the amplification of mRNA and the quantification of the amplification product of said mRNA, such as electrophoresis and staining, or alternatively, by means of Northern blot and the use of suitable probes, Northern blot and use of specific probes of the mRNA of the genes of interest or of their corresponding cDNA/cRNA, mapping with the SI nuclease, RT-PCR, hybridization, microarrays, etc. Similarly, the levels of the cDNA/cRNA corresponding to said mRNA encoded by the marker genes can also be quantified by means of using conventional techniques; in this event, the method of the invention includes a step of synthesis of the corresponding cDNA by means of reverse transcription (RT) of the corresponding mRNA followed by the synthesis (RNA polymerase) and amplification of the cRNA complementary to said cDNA. Conventional methods of quantifying the expression levels can be found in laboratory manuals.

In order to normalize the values of mRNA expression among the different samples, it is possible to compare the expression levels of the mRNA of interest in the test samples with the expression of a control RNA. A "control RNA" as used herein, relates to RNA whose expression levels do not change or change only in limited amounts. Preferably, the control RNA is mRNA derived from housekeeping genes and which code for proteins which are constitutively expressed and carry out essential cellular functions. Preferred housekeeping genes for use in the present invention include 18-S ribosomal protein, β-2-microglobulin, ubiquitin, cyclophilin, GAPDH, PSMB4, tubulin and β-actin.

Alternatively, it is also possible to determine the expression levels of the marker genes by means of the determination of the expression levels of the proteins encoded by said genes, since if the expression of genes is increased, an increase of the amount of corresponding protein should occur and if the expression of genes is decreased, a decrease of the amount of corresponding protein should occur.

The determination of the expression levels of the proteins can be carried out by qualitative and/or quantitative tests selected from the group consisting of an immunological test, bioluminescence, fluorescence, chemiluminescence, electrochemistry and mass spectrometry. Particular tests that can be implemented in a point of care test format (POCT) are recommended to make easy and fast the determining of marker levels. In a particular embodiment, point of care tests include lateral flow tests, which allow detecting the presence (or absence) of a target analyte in liquid sample (matrix) without the need for specialized and costly equipment, though many lab-based applications exist that are supported by reading equipment.

As will be illustrated in examples, a particular POCT was developed and it was tested in ambulances and helicopters. By means of this POCT useful high sensitivity rates at 100% of specificity for ischemic strokes were achieved, that allowed initiating pre-hospital reperfusion therapies in selected cases much faster than using standard technologies.

Independently of the test format, particular quantitative tests are selected from the group consisting of an immunological test, bioluminescence, fluorescence, chemiluminescence, electrochemistry and mass spectrometry.

In one embodiment, the level of expression is determined by immunological techniques such as enzyme-linked immunosorbent assay (ELISA), enzyme immunodot assay, agglutination assay, antibody-antigen-antibody sandwich assay, antigen-antibody-antigen sandwich assay, immunocromatography, or other immunoassay formats well-known to the ordinarily skilled artisan, such as radioimmunoassay, as well as protein microarray formats, such as single molecular assay (SIMOA), Western Blot or immunofluorescence.

Western blot is based on the detection of proteins previously resolved by gel electrophoreses under denaturing conditions and immobilized on a membrane, generally nitrocellulose by the incubation with an antibody specific and a developing system (e.g. chemoluminiscent). The analysis by immunofluorescence requires the use of an antibody specific for the target protein for the analysis of the expression. ELISA is based on the use of antigens or antibodies labelled with enzymes so that the conjugates formed between the target antigen and the labelled antibody results in the formation of enzymatically-active complexes. Since one of the components (the antigen or the labelled antibody) are immobilised on a support, the antibody-antigen complexes are immobilised on the support and thus, it can be detected by the addition of a substrate which is converted by the enzyme to a product which is detectable by, e.g. spectrophotometry, fluorometry, mass spectrometry or tandem mass tags (TMT). SIMOA is a type of assay more sensitive than an ELISA, since it uses arrays of femtoliter-sized reaction chambers, which are termed single-molecule arrays (Simoa™) that can isolate and detect single enzyme molecules. Because the array volumes are approximately 2 billion times smaller than a conventional ELISA, a rapid build-up of fluorescent product is generated if a labeled protein is present. With diffusion defeated, this high local concentration of product can be readily observed. Only a single molecule is needed to reach the detection limit. Using the same reagents as a conventional ELISA, this method has been used to measure proteins in a variety of different matrices (serum, plasma, cerebrospinal fluid, urine, cell extracts, etc.) at femtomolar (fg/mL) concentrations, offering a roughly 1000-fold improvement in sensitivity.

On the other hand, the determination of the protein expression levels can be carried out by constructing a tissue microarray (TMA) containing the subject samples assembled, and determining the expression levels of the proteins by techniques well known in the state of the art.

In a preferred embodiment the determination of the levels of the markers are determined by immunological technique. In a more preferred embodiment, the immunological technique is ELISA.

When an immunological method is used, any antibody or reagent known to bind with high affinity to the target proteins can be used for detecting the amount of target proteins. It is preferred nevertheless the use of antibody, for example polyclonal sera, hybridoma supernatants or monoclonal antibodies, antibody fragments, Fv, Fab, Fab' y F(ab') 2, ScFv, diabodies, triabodies, tetrabodies and humanised antibodies.

As previously cited, the expression levels of the NT-proBNP and/or RBP4 and/or GFAP can be determined by measuring both the levels of protein, and the levels of variants thereof, such as fragments, isoforms, analogues and/or derivatives.

The term "functionally equivalent variant" is understood to mean all those proteins derived from NT-proBNP and/or RBP4 and/or GFAP sequence by modification, insertion and/or deletion or one or more amino acids, whenever the function of said variants are substantially maintained. Preferably, variants of NT-proBNP and/or RBP4 and/or GFAP are (i) polypeptides in which one or more amino acid residues are substituted by a preserved or non-preserved amino acid residue (preferably a preserved amino acid residue) and such substituted amino acid may be coded or not by the genetic code, (ii) polypeptides in which there is one or more modified amino acid residues, for example, residues modified by substituent bonding, (iii) polypeptides resulting from alternative processing of a similar mRNA, (iv) polypeptide fragments and/or (v) polypeptides resulting from NT-proBNP and/or RBP4 and/or GFAP fusion or the polypeptide defined in (i) to (iii) with another polypeptide, such as a secretory leader sequence or a sequence being used for purification (for example, His tag) or for detection (for example, Sv5 epitope tag). The fragments include polypeptides generated through proteolytic cut (including multisite proteolysis) of an original sequence. The variants may be post-translationally or chemically modified. Such variants are supposed to be apparent to those skilled in the art.

As known in the art the "similarity" between two proteins is determined by comparing the amino acid sequence and its conserved amino acid substitutes of one protein to a sequence of a second protein. The variants are defined to include polypeptide sequences different from the original sequence, preferably different from the original sequence in less than 40% of residues per segment concerned, more preferably different from the original sequence in less than 25% of residues per segment concerned, more preferably different from the original sequence in less than 10% of residues per segment concerned, more preferably different from the original sequence in only a few residues per segment concerned and, at the same time, sufficiently homologous to the original sequence to preserve functionality of the original sequence. Variants according to the present invention includes amino acid sequences that are at least 60%, 65%, 70%, 72%, 74%, 76%, 78%, 80%, 90%, or 95% similar or identical to the original amino acid sequence. The degree of identity between two proteins is determined using computer algorithms and methods that are widely known for the persons skilled in the art. The identity between two amino acid sequences is preferably determined by using the BLASTP algorithm [BLASTManual, Altschul, S., et al, NCBI NLM NIH Bethesda, Md. 20894, Altschul, S., et al, J. Mol. Biol. 215: 403-410 (1990)].

The proteins can be post-translationally modified. For example, post-translational modifications that fall within the scope of the present invention include signal peptide cleavage, glycosylation, acetylation, isoprenylation, proteolysis myristoylation, protein folding and proteolytic processing, etc. Additionally, the proteins may include unnatural amino acids formed by post-translational modification or by introducing unnatural amino acids during translation.

In another particular embodiments of the in vitro methods of the invention that provide a differential diagnostic and information for selecting a therapy, they further comprise the steps of (i) collecting the diagnostic information, and (ii) saving the information in a data carrier.

In the sense of the invention a "data carrier" is to be understood as any means that contain meaningful information data for the differential diagnosis of IS and ICH and/or for the selection of a candidate to reperfusion therapy, such as paper. The carrier may also be any entity or device capable of carrying the differential diagnosis data or information for selecting a therapy. For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal, which may be conveyed via electrical or optical cable or by radio or other means. When the diagnosis/therapy selection data are embodied in a signal that may be conveyed directly by a cable or other device or means, the carrier may be constituted by such cable or other device or means. Other carriers relate to USB devices and computer archives. Examples of suitable data carrier are paper, CDs, USB, computer archives in PCs, or sound registration with the same information.

The invention also encompasses an in vitro method for the prognosis of a patient suffering ischemic stroke, comprising determining the level of retinol binding protein-4 (RBP4) and N-terminal fragment of B-type natriuretic peptide (NT-proBNP) in an isolated sample of said patient.

In a particular embodiment of the in vitro method for the prognosis, the levels of at least RBP4 or the two proteins are compared with a reference value, wherein said reference value is selected from a value or range of values indicating or confirming that the subject is suffering ischemic stroke. In another more particular embodiment, the prognosis is defined by a dependency degree greater than 2 according to modified ranking score (mRS), and determined within 1-5 months after stroke onset; and/or as having a prognosis defined by a three-month after onset mortality rate comprised from 20% to 30%.

As previously indicated, the invention also relates to kits comprising reagent means for detecting the level of a RBP4 and NT-proBNP.

In a particular embodiment of the kits of the invention, they further comprise reagent means for detecting the level of GFAP.

The term "kit", as used herein, refers to a product containing the different reagents (or reagent means) necessary for carrying out the methods of the invention packed so as to allow their transport and storage. Materials suitable for packing the components of the kit include crystal, plastic (e.g. polyethylene, polypropylene, polycarbonate), bottles, vials, paper, or envelopes.

Additionally, the kits of the invention can contain instructions for the simultaneous, sequential or separate use of the different components which are in the kit. Said instructions can be in the form of printed material or in the form of an electronic support capable of storing instructions susceptible of being read or understood, such as, for example, electronic storage media (e.g. magnetic disks, tapes), or optical media (e.g. CD-ROM, DVD), or audio materials. Additionally, or alternatively, the media can contain internet addresses that provide said instructions.

The reagent means (or simply reagents) of the kit include compounds that bind specifically to the marker proteins. Preferably, said compounds are antibodies, aptamers or fragments thereof.

In a preferred embodiment, the reagent is an antibody or fragments thereof. Thus, the reagent means are one or more antibodies that specifically recognize the proteins of interest (i.e NT-proBNP, RBP4 and if determined GFAP). The antibodies of the kit of the invention can be used according to techniques known in art for determining the protein expression levels, such as, for example, flow cytometry, Western blot, ELISA, RIA, competitive EIA, DAS-ELISA, techniques based on the use of biochips, protein microarrays, or assays of colloidal precipitation in reactive strips.

The antibodies can be fixed to a solid support such as a membrane, a plastic or a glass, optionally treated to facilitate the fixation of said antibodies to the support. Said solid support comprises, at least, a set of antibodies which specifically recognize the marker (i.e. the protein of interest), and which can be used for detecting the levels of expression of said marker.

Additionally, the kits of the invention comprise reagents for detecting a protein encoded by a constitutive gene. The availability of said additional reagents allows normalizing the measurements performed in different samples (for example, the sample to be analyzed and the control sample) to rule out that the differences in the expression of the biomarkers are due to a different quantity of total protein amount in the sample more than the real differences in the relative levels of expression. The constitutive genes in the present invention are genes that are always active or being transcribed constantly and which encode for proteins that are expressed constitutively and carry out essential cellular functions. Proteins that are expressed constitutively and can be used in the present invention include, without limitation, $\beta$-2-microglobulin (B2M), ubiquitin, 18-S ribosomal protein, cyclophilin, GAPDH, PSMB4, tubulin and actin.

In a preferred embodiment, the reagent means for assaying the levels of the different biomarkers comprise at least 10%, at least 20%, at least 30%, at least 40%, at least 50%, at least 60%, at least 70%, at least 80%, at least 90% or at least 100% of the total amount of reagents for assaying biomarkers forming the kit. Thus, in the particular case of kits comprising reagents for assaying the levels of RBP4, NT-proBNP and optionally GFPA, the reagents specific for said biomarkers (i.e. antibodies which bind specifically to RBP4, NT-proBNP and optionally GFPA) comprise at least 10%, at least 20%, at least 30%, at least 40%, at least 50%, at least 60%, at least 70%, at least 80%, at least 90% or at least 100% of the antibodies present in the kit. These kits are, thus, simplified kits including mainly the reagent means for detecting the levels of the two (or three) proteins.

In another particular embodiment, the kits of the invention are conceived as point of care tests. More in particular they are in form of lateral flow tests.

In another particular embodiment the kit according to the invention comprises a support and one or more sample inlet ports for deposition of a biofluid sample, in particular whole blood; a reaction area comprising the means/reagents that bind specifically to the marker proteins, in particular antibodies; and wherein the sample inlet port is connected with the reaction area. In another more particular embodiment, the kit comprises as many sample inlet ports as markers (one, two or three) to be detected and corresponding reaction areas connected thereto. In another embodiment the kit comprises one single inlet import and as capillary tracks connecting to as many reactive areas, said capillary tracks conducting part of the sample to each corresponding connected reaction area. The kits comprising more than one reaction areas are multiplex kits.

In another aspect, the invention relates to the use of the kit of the invention for differentiating IS from ICH or for selecting a patient suffering stroke for a reperfusion therapy, said reperfusion therapy being, in a particular embodiment, selected from the group consisting of a therapy with an antithrombotic agent, thrombectomy and a combination thereof.

Thus, in a particular embodiment, the invention relates to the use of the kit of the invention in any of the methods of the invention.

As illustrated in examples below, inventors surprisingly found that the determining in combination of the levels of RBP4 and of NT-proBNP, an optionally of those of GFAP and/or certain additional clinical parameters, allowed the diagnosis of those stroke suffering patients with a large vessel occlusion (LVO). LVO is likely in part responsible of the previously commented poor outcome or bad prognosis of the ischemic stroke patients.

Thus, related with this selection and correct classification of the stroke suffering patients, invention also relates to an in vitro method for the diagnosis of LVO, comprising determining the level of RBP4 and of NT-proBNP in an isolated sample of a subject. In a particular embodiment, the subject is an ischemic stroke patient.

In a particular embodiment of the in vitro method for the diagnosis of LVO, it further comprises determining the level of GFAP. In another more particular embodiment, the method further comprises he step of comparing the levels of RBP4, NT-proBNP and if determined of GFAP, with a corresponding reference value, wherein said reference value or interval is selected from a value or interval of values from a subject suffering from LVO, and wherein the subject is diagnosed as LVO when at least the level of one of RBP4, NT-proBNP and GFAP are both within the value or interval of values from a subject suffering from LVO. Even in a more particular embodiment of of the in vitro method for the diagnosis of LVO, it comprises determining one or more clinical parameters. These clinical parameters are, in particular, selected from the group consisting of blood pressure, including systolic blood pressure and/or diastolic blood pressure, glycemia, levels of blood d-dimer, age, scores from systematic assessment tools of stroke-related neurologic deficits, gender, and combinations thereof. In a more particular embodiment, the in vitro method for the diagnosis of LVO, comprises determining the level of RBP4, NT-proBNP and GFAP, glycemia, d-dimer in the isolated sample and further diastolic blood pressure and baseline score from systematic assessment tools of stroke-related neurologic deficits, such as NIHSS-score, RACE, Cincinnati, LAMS, etc. As in other aspects and embodiments, the isolated sample is preferably a biofluid and more in particular is selected from plasma and serum. Also as disclosed for other aspects of the invention, the values of the clinical parameters can be used in combination with the levels of RBP4, NT-proBNP and optionally of GFAP in adequate algorithms for correctly classifying the patient as suffering from LVO. In another particular embodiment of the in vitro method for the diagnosis of LVO, the determining of the level of RBP4 and of NT-proBNP, and if determined of GFAP, is carried out within the two first hours after the stroke onset, more in particular within the first hour after the stroke onset.

According to inventor's knowledge, this is the first time a combination of markers in serum and/or plasma gives reliable information for the accurate diagnosis of LVO (high sensitivity among IS patients). This supposes another real contribution to the art, since nowadays clinical scores or protocols are used, which are far from values of 100% sensitivities and which do not have proper accuracy, reason of why they are not well implemented in the clinical practice.

The high sensitivity in the diagnosis of LVO in ischemic stroke patients, associated to the determination of the above-mentioned levels of RBP4, NT-proBNP and optionally of GFAP, allows deriving these patients to the nearest reference hospital in which mechanical thrombectomy can be applied.

Therefore, with a fast good classification of the patients manifesting stroke symptoms using the levels of RBP4, NT-proBNP and optionally of GFAP, for example at ambulance level and if possible within the first two hours after onset, even within the first hour, the patient can be classified as candidate for reperfusion to receive first an antithrombotic agent at ambulance, and be derived to the hospital with the facilities to treat LVO.

It is also disclosed herewith an in vitro method for differentiating ischemic stroke from haemorrhagic stroke in a patient, or for selecting a patient suffering stroke for a reperfusion therapy, comprising determining the level of NT-proBNP and the level of GFAP in an isolated sample of the patient, optionally in combination with a clinical parameter selected from the group consisting of blood pressure, including systolic blood pressure and/or diastolic blood pressure, glycemia, age, NIHSS scores from systematic assessment tool stroke-related neurologic deficit, gender, and combinations thereof. More in particular, the method comprises determining the level of NT-proBNP and the level of GFAP in the isolated sample, in combination with blood pressure of the patient. This particular combination allows a discrimination with high sensitivity and specificity, as will be depicted in Examples below. In another more particular embodiment, the method comprises determining also the level of RBP4 in the isolated sample. More in particular, isolated sample is selected from a biopsy sample, tissue, cell or biofluid (plasma, serum, saliva, semen, sputum, cerebral spinal fluid (CSF), tears, mucus, sweat, milk, and brain extracts. In particular is serum or plasma.

All particular embodiments previously disclosed for the first and second aspects do also apply to this method for differentiating ischemic stroke from haemorrhagic stroke in a patient, and/or for selecting a patient suffering stroke for a reperfusion therapy, the method comprises the step of comparing the levels of NT-proBNP and of GFAP.

In a more particular embodiment the of in vitro method for differentiating ischemic stroke from haemorrhagic stroke in a patient, and/or for selecting a patient suffering stroke for a reperfusion therapy, the method comprises the step of comparing the levels of NT-proBNP and of GFAP, with a corresponding reference value or reference interval for each protein, said reference value or interval selected from a value or interval of values from a subject suffering from ischemic stroke, and wherein the subject is classified as a candidate for a reperfusion therapy when at least the level of GFAP and of NT-proBNP are both within the value or interval of values from a subject suffering from ischemic stroke, and optionally blood pressure is also within the values of a subject suffering from ischemic stroke. In another particular embodiment, and as indicated before for other aspects of the invention, the values of the levels in the isolated sample of NT-proBNP and of GFAP, are used in combination with determined blood pressure in adequate algorithms for correctly classifying the patient as candidate to reperfusion therapy. Blood pressure within a certain interval in combination with certain levels of the two proteins are used in a decision protocol for the correct classification and selection of therapy. The values are, in another particular embodiment, introduced in formulas of regression models to give a score or final value allowing such classification. In order to increase sensitivity of the method, the determining of the levels of NT-proBNP and of GFAP is carried out within the two first hours after the stroke onset. More in particular within the first hour. In another particular embodiment, high sensitivity for the detection of ischemic stroke with large vessel occlusion, thus as candidates to the particular thrombectomy therapeutic approach, is achieved when the levels of NT-proBNP and of GFAP are determined and values are used in combination with clinical variables such as baseline NIHSS score and/or d-dimer levels in blood, and/or blood pressure values. In another particular embodiment of the in vitro method for differentiating ischemic stroke from haemorrhagic stroke in a patient, or for selecting a patient suffering stroke for a reperfusion therapy, comprising determining the level of NT-proBNP and the level of GFAP in an isolated sample of the patient, the levels are measured with a POCT including (comprising) reagent means for the analysis of these two proteins in the isolated sample. More in particular, this kit comprises among the reagent means, only those means for detecting the level (either protein level or mRNA level) of one or both of NT-proBNP and GFAP.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

In order to provide a method for pre-hospital differentiation between ischemic strokes (IS) and intracerebral hemorrhage (ICH) using blood biomarkers, inventors carried out an extensive analysis of samples of stroke patients at hand. Main aim was to find reliable markers giving information to start a reperfusion therapy (mainly intravenous thrombolysis) without the need of neuroimaging techniques.

Example 1. Classification of Patients and Selection of Therapy in Two Different Cohorts (Cohort 1 with of 190 Patients; Cohort 2 with 67 Patients)

Materials and Methods

From December-2013 to July-2014, patients with suspected stroke admitted within 4.5 hours after stroke onset were enrolled. Blood samples were collected at admission (baseline). Biomarkers were mainly measured by ELISA and SIMOA. Stroke subtype was confirmed by neuroimaging techniques. Biomarkers were dichotomized by cut-offs, selected as having the highest sensitivity with 100% specificity for IS in order to minimize any mistake by giving tPA to an ICH patient.

The patient cohorts were as follows:

Cohort 1 (ELISA cohort): 190 patients who have suffered stroke (155 ischemic, 35 hemorrhagic).

Cohort 2 (SIMOA cohort): 67 patients who have suffered stroke (33 ischemic, 34 hemorrhagic).

Kits for analysis of markers were:

for RBP4→cat #DRB400, Quantikine R&D Systems;

for GFAP (measured using a Simoa kit and giving the name of SIMOA cohort to Cohort 2)→cat #102336 and consumables:

Simoa Accelerator—1 Plate Lab Service Fee, cat #100835

Accelerator Consumables Kit, cat #ACC1001 for NT-proBNP→following reference catalogue reactives where used in an automated Roche® system (4842464130-proBNP GEN.2 ELECSYS; 4917049922-Precicontrol cardiac G4; 4842472190—CALSET proBNO GEN.2 ELECSYS)

These cohorts 1 and 2 were selected after exclusion of mimics, those patients not suffering from stroke but having clinical signs of stroke.

In all patients the level of expression at baseline of GFAP, NT-proBNP and RBP4 was measured using ELISA techniques (for NT-proBNP and RBP4; see above) or SIMOA (for GFAP, see above).

Different methods for the analysis of retrieved data were assayed: Basic cut-offs (method 1), a Principal component analysis (PCA) (method 2), an improved (more rounds) of the PCA; and a support vector machine procedure (SVM) (method 4).

In all methods, the concern here was to find optimal cut-offs of these blood biomarkers values, which could indicate an exact value of each biomarker where it could be assured that patients were classified with 100% accuracy in order to avoid any mistake, since the offering of reperfusion therapies (i.e. tPA or TNK) to ICH patients might have fatal side effects.

Results

Method 1 (Basic Cut-Offs)

In this method the simplest cut-offs for a unique biomarker in training cohorts was used, and then all the cut-offs were combined to obtain a final classification.

In Cohort 1 (ELISA cohort) Ischemic patients could be detected by looking at those who had either high levels of NT-proBNP or RBP4. So, looking for 100% specificity, patients were classified as ischemic if they had:

NT-proBNP>4062 pg/mL. 100% specificity and 14.3% sensibility were obtained (22/155) ischemic patients were detected without risk) (see FIG. 1 (A)) or RBP4>52 µg/mL. 100% specificity and 6.5% sensibility were obtained (10/155 ischemic patients were detected without risk) (see FIG. 1(B))

Just one of these 2 conditions was needed to be fulfilled. At the end, 31/155 ischemic patients were classified (20.1%) with 100% specificity if both conditions were simultaneously fulfilled (see FIG. 1(C)).

Data are depicted in FIG. 1, wherein a cut-off (dark line in both panels A and B) of 4062 pg/ml for NT-proBNP or a cut-off of 52 µg/mL for RBP4 allowed a reliable discrimination between IS and ICH. In panel C, log 10(NT-proBNP) and RBP4 levels were simultaneously plotted with the corresponding previously determined cut-offs for each protein.

With cohort 2 (67 patients) including determination of GFAP using SIMOA test for this protein (herewith termed also SIMOA cohort) a first approach was done to combine GFAP with the other biomarkers in order to perform a safe and better detection of ischemic patients.

The classification had 2 phases. First, those who had values of GFAP<325 ng/mL as a first condition were selected as possible ischemic candidates. 27 hemorrhagic patients, and only 6 ischemic patients from the potential ischemic patients were discarded. Visual presentation of this first discrimination step is plotted in FIG. 2 (A), wherein the 3D graph classifies patients according to detected levels of GFAP (as log(GFAP), the levels of NT-proBNP (as log(NT-proBNP) and the levels of RBP4. Values under the square defining values of GFAP<325 ng/mL (3D space signalized by an arrow) correspond to those of selected patients as ischemic candidates in the first phase.

As a second condition patients as ischemic were those who had either:

NT-proBNP>1305 pg/mL. 100% specificity and 30.3% sensibility were obtained (10/33 ischemic patients detected), or RBP4>38 µg/mL. 100% specificity and 30.3% sensibility were obtained (10/33 ischemic patients detected).

Figure 2:
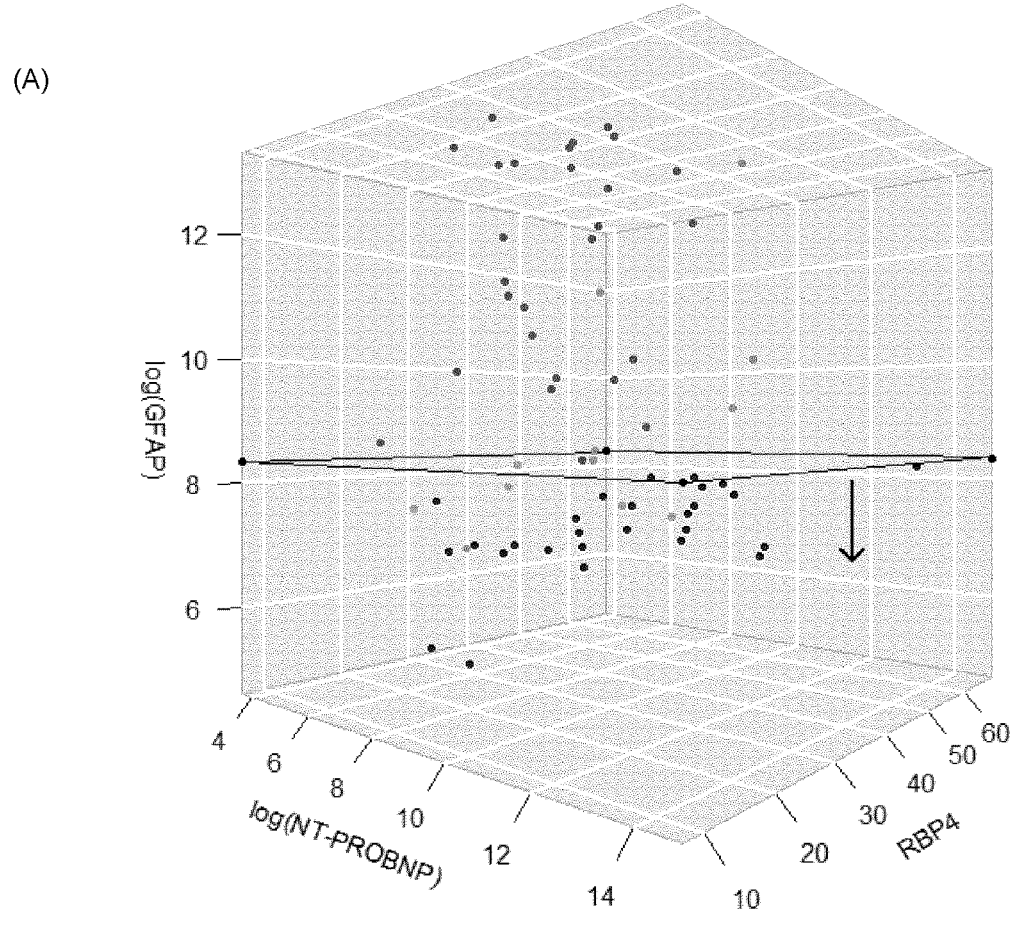
FIG. 2 shows in (A) the cut-off level for GFAP (log (GFAP)) of >325 pg/ml in a different cohort of patients. In panel (B), the log 10(NT-proBNP) and RBP4 levels were simultaneously plotted with the corresponding previously determined cut-offs for each protein in this cohort of patients. 100% specificity IS has the same meaning as in FIG. 1.
Figure 2:
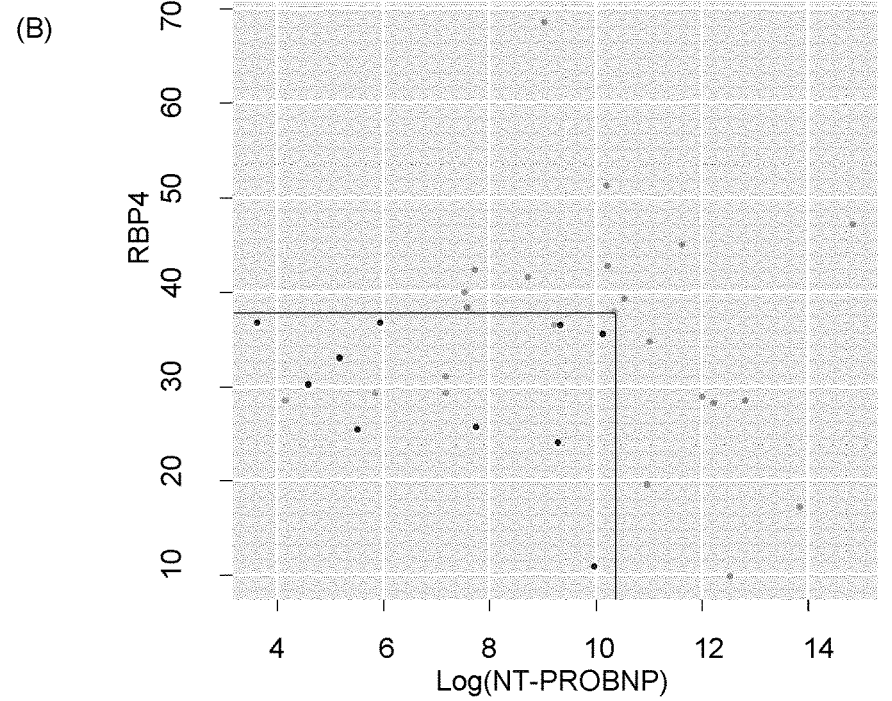

If GFAP was not considered anymore in possible ischemic candidates selected in first phase and those patients with NT-proBNP>1305 pg/mL and RBP4>38 µg/mL were considered as candidates, then 17/33 ischemic patients (51.5%) without any risk (100% specificity) were detected. Data are depicted in FIG. 2 (B).

Several analysis were done at different specificity values (different from 100%)

At 97% specificity ischemic patients were those who had values of GFAP<325 ng/mL and:

NT-proBNP>600 pg/mL. 100% specificity and 51.5% sensibility were obtained (17/33 ischemic patients were detected)

RBP4>36.6 µg/mL. 97% specificity and 39.4% sensibility were obtained (13/33 ischemic patients were detected)

This allowed detecting 23/33 ischemic patients (69.7%) with a 97% specificity.

At 94% specificity ischemic patients were those who had values of GFAP<325 ng/mL and:

NT-proBNP>147 pg/mL. 94% specificity and 69.7% sensibility were obtained (23/33 ischemic patients were detected)

RBP4>31 µg/mL. 94% specificity and 51.5% sensibility were obtained (17/33 ischemic patients were detected)

This allowed detecting 26/33 ischemic patients (78.7%) with a 94% specificity.

Cut-off values imply always a deviation or certain variability due to different factors. All those herewith indicated relate to a particular fix predictive accuracy (usually IC 95%), so that they are within a range of also considered positive or discriminating values.

Using method 1 the best cut-off for reliably classifying stroke patients were the individual cut-offs of ELISA cohort (RBP4>52 µg/ml and NT-proBNP>4062.0 pg/ml)

Method 2 (Principal Component Analysis)

Using the PCA computation it was seen which of these 3 biomarkers explains the most variability in less principal components (Jolliffe, I. T. (2002). Principal Component Analysis, second edition (Springer), ISBN 0-387-95442-2). The procedure consisted on performing a Principal Component Analysis. After it was computed, it was seen which variables contributed the most with Principal Components, the results were that GFAP was the variable which correlated the most with PC1 and RBP4 was the variable which correlated the most with PC2. So, in order to classify the patients, the best order to follow will be GFAP>RBP4>NT-proBNP.

Briefly, Principal component analysis (PCA) is a statistical procedure that uses an orthogonal transformation to convert a set of observations of possibly correlated variables (entities each of which takes on various numerical values) into a set of values of linearly uncorrelated variables called principal components. If there are n observations with p variables, then the number of distinct principal components is min(n-1,p). This transformation is defined in such a way that the first principal component has the largest possible variance (that is, accounts for as much of the variability in the data as possible), and each succeeding component in turn has the highest variance possible under the constraint that it is orthogonal to the preceding components. The resulting vectors (each being a linear combination of the variables and containing n observations) are an uncorrelated orthogonal basis set. PCA is sensitive to the relative scaling of the original variables. PCA is mostly used as a tool in exploratory data analysis and for making predictive models. PCA is mathematically defined as an orthogonal linear transformation that transforms the data to a new coordinate system such that the greatest variance by some projection of the data comes to lie on the first coordinate (called the first principal component), the second greatest variance on the second coordinate, and so on.

This order of cut-off biomarkers (GFAP>RBP4>NT-proBNP) was used to classify patients. First GFAP cut-off was used, classifying the maximum number of patients with 100% sensitivity or 100% specificity. Then the RBP4 cut-off was used to classify with 100% sensitivity or 100% specificity the patients that couldn't be classified in the previous cut-off. Finally, the NT-proBNP cut-off was used to classify with 100% sensitivity or 100% specificity the patients that weren't classified yet. Once these 3 cut-offs were applied it was considered a completed 1$^{st}$ round of cut-offs.

The same analysis was done again using only 2 biomarkers (RBP4 and NT-proBNP).

In this case when using GFAP the cut-offs were illustrated in Table 1:

TABLE 1

| Classification of patients with PCA analysis (1$^{st}$ round) | |
| --- | --- |
| Hemorrhagic | Ischemic |
| GFAP > 0.179 ng/mL RBP4 < 8.619 µg/mL | RBP4 > 51.988 µg/mL (ELISA cohort or also named cohort 1) RBP4 > 60.199 ug/mL (SIMOA cohort 2) NT-proBNP > 4076.5 pg/mL (ELISA cohort) NT-proBNP > 3984 pg/mL (SIMOA cohort or also named cohort 2) |

Cohort 1 (190 patients) cut-off was more robust than that which was found using cohort 2, in which besides the determination of NT-proBNP and RBP4 using ELISA test, also GFAP was determined using a SIMOA test (i.e. the SIMOA cohort (67 patients)).

Using cut-off of ELISA cohort (cohort 1) it was possible to classify with 100% sensitivity or 100% specificity a 23.16% of the entire cohort (37.14% for Hemorrhagic patients, 20% for Ischemic patients).

Using cut-off of SIMOA cohort (cohort 2) it was possible to classify with 100% sensitivity or 100% specificity a 31% of the entire cohort (38% Hemorrhagic patients, 24% Ischemic patients).

Using few individuals in cohort 2 allowed differentiating them better (classifying almost an 1% more of Hemorrhagic patients and a 4% more of Ischemic ones).

Using only RBP4+NT-proBNP the cut-offs were those of Table 2:

TABLE 2

| Classification of patients with PCA analysis (1$^{st}$ round) | |
| --- | --- |
| Hemorrhagic | Ischemic |
| RBP4 < 8.619 µg/mL | RBP4 > 51.988 µg/mL (ELISA cohort, also named cohort 1) RBP4 > 60.199 µg/mL (SIMOA cohort also named cohort 2) NT-proBNP > 4076.5 pg/mL (ELISA cohort) NT-proBNP > 3984 pg/mL (SIMOA cohort) |

Cohort a (190 patients) was again more robust than cohort 2 (67 patients). (The same cut-offs as above)

Using cut-offs from ELISA cohort (cohort 1) it was possible to classify with 100% sensitivity or 100% specificity a 16.8% of the entire cohort (3% for Hemorrhagic patients, 20% for Ischemic patients).

Using cut-offs from SIMOA cohort (cohort 2) it was possible to classify with 100% sensitivity or 100% specificity a 13.4% of the entire cohort (3% Hemorrhagic patients, 24% Ischemic patients).

Using few individuals in the SIMOA cohort allowed differentiating them better (classifying a 4% more of Ischemic patients).

Method 3 (Principal Component Analysis)

This method was an extension of method 2, where more rounds with non-classified individuals were computed.

After the 1$^{st}$ round completion a logistic regression was performed to check if there was still a tendency with some biomarker related to the outcome. After that cut-offs were computed again in the same order with the patients that were not classified yet.

This method was performed till no tendency was observed or it was not possible to classify more individuals with 100% sensitivity or 100% specificity. It's important to remark that it has to be followed the order of the cut-offs from the 1st one to the last once the individual has been classified.

Method 3 was performed also with only 2 biomarkers (RBP4 and NT-proBNP).

With ELISA cohort (cohort 1) and using as biomarkers: GFAP, RBP4 and NT-proBNP, the following cut-offs were obtained:

TABLE 3

| Classification of patients with PCA analysis (more than one rounds) | | |
|---|---|
| | Hemorrhagic | Ischemic |
| Round 1 | GFAP > 0.179 ng/mL RBP4 < 8.619 µg/mL | RBP4 > 51.988 µg/mL NT-proBNP > 4076.5 pg/mL |
| Round 2 | | GFAP > 0.0995 ng/mL RBP4 <13.157 µg/mL NT-proBNP > 1312.5 pg/mL |
| Round 3 | GFAP > 0.0505 ng/mL NT-proBNP > 1219.5 pg/mL | RBP4 < 15.488 µg/mL NT-proBNP > 920.2 pg/mL |
| Round 4 | RBP4 < 19.262 µg/mL | |

With this method 51% of the individuals were classified with 100% sensitivity or specificity (60% for hemorrhagic and 49% for ischemic).

With ELISA cohort (cohort 1), using as biomarkers RBP4 and NT-proBNP the following cut-offs were obtained:

TABLE 4

| Classification of patients with PCA analysis (more than one rounds) | | |
|---|---|
| | Hemorrhagic | Ischemic |
| Round 1 | RBP4 < 8.619 µg/mL | RBP4 > 51.988 µg/mL NT-proBNP > 4076.5 pg/mL |
| Round 2 | RBP4 > 51.877 µg/mL | RBP4 < 13.157 µg/mL NT-proBNP > 1468.5 pg/mL |
| Round 3 | | RBP4 > 46.19 µg/mL |

36.5% of the individuals with 100% sensitivity or specificity (6% for hemorrhagic and 44% for ischemic).

Method 4 (SVM)

RBP4 and NT-proBNP levels were computed using a Support Vector Machines procedure (SVM) in order to maximize the number of IS patients well classified when classifying with 100% specificity all the ICH patients (See "A User's Guide to Support Vector Machines", Article in Methods in Molecular Biology, (Clifton N.J.), 2010, Asa Ben-Hur and Jason Weston). Radial kernel analysis was used, and the parameters were as follows: $c=100$ and sigma$=0.05$. To obtain a classifier with 100% specificity in data for ICH the decision value should have to be increased in each point on 0.71 (the intuition behind the decision value is that the more positive value we have the less chances to classify an ICH patient as IS while losing chances to classify an IS patient as IS).

With this method a 29.7% sensibility was achieved for IS.

Figure 3:
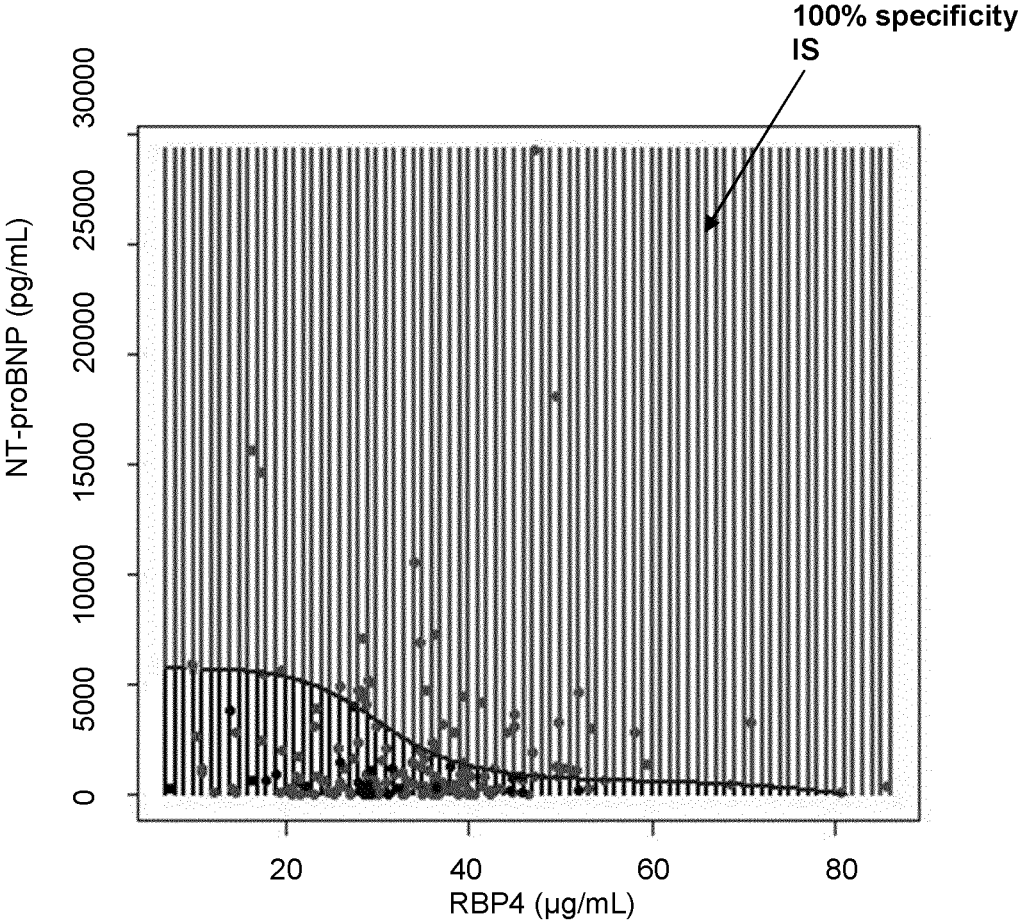
FIG. 3 is a graphic resulting from the analysis of retrieved data with a Support Vector Machine procedure (SVM). Values over the sigmoidal curve are 100% IS, and values under the curve correspond to patients with any of ICH or IS subtypes. Y-axis levels of NT-proBNP (pg/mL); X-axis levels of RBP4 (µg/mL). "can be introduced in a support vector machine procedure with a gaussian kernel". 100% specificity IS has the same meaning as in FIG. 1.

Data are depicted in FIG. 3, wherein values over the "sigmoidal curve" are 100% IS (signalized with an arrow), and values under the curve correspond to patients with any of ICH or IS subtypes.

As can be derived from this FIG. 3, the combination of the levels of RBP4 and NT-proBNP allowed good classification of patients and the proper selection of therapy. Said levels can be introduced in a support vector machine procedure with a gaussian kernel, giving a graph as in FIG. 3 and, depending on the value of one of the proteins, correct classification of a patient as IS or ICH will result from the value of the other protein.

According to SVM, once the determined values of a tested sample are obtained, they are introduced in the trained SVM that gives back a decision value that allows classification of the test sample to one category (IS) or another (ICH). In particular, said decision value usually is 0.5 and if needed it can be accommodated to improve correct classification of subjects. Over this value the patient is classified in one category and under in the other, depending on the trained machine. Decision value can be accommodated.

Conclusions

Using method 1 (basic cut-offs) with ELISA cohort (cohort 1) and using RBP4 and NT-proBNP separately allowed proper discrimination of a 6.5% and 14.2% of IS respectively with 100% specificity for ICH. When used together discrimination rose to a 20% of IS patients with 100% specificity for ICH, which is less than the sum of both biomarkers separately (the reason of that is that 1 individual is classified properly by both biomarkers). In SIMOA cohort (cohort 2): When GFAP cut-off was used to separate the maximum number of ICH and IS patients and then trying to classify the IS patients within the bottom of the GFAP cut-off, sensitivity for IS patients was increased (51.5%) while 100% specificity was maintained for ICH patients.

Using method 2 (also known as classify-remove) and Method 3 (also known classify—remove—repeat), allowed observing that addition of GFAP biomarker just helped to classify properly ICH patients (60% when using GFAP compared to a 6% when don't use GFAP in ELISA cohort and 37% when using GFAP compared to a 3% when don't use GFAP in values for SIMOA cohort). It's also important to remark that it was not lost a high amount of power to classify IS patients when GFAP was not used (49% vs 44% in values with ELISA cohort and 24% vs 24% in values with SIMOA cohort, when using or not GFAP biomarker).

The inclusion of GFAP doesn't influence the power of discrimination for IS patients.

Finally, using method 4 (SVM) classifier, which is a more sophisticated method it was possible to discriminate properly a 29.7% of IS patients with 100% specificity for ICH.

All these data make also clear that reference values for correct classification of patients are dynamic values, which can be a function of several parameters, such as the number of other markers that are simultaneously determined, or the technology used for data analysis from cohorts of patients. On the other hand, for a fixed amount or level of one of the proteins, the amount of other simultaneously markers determined with the first and allowing a good classification can vary and be represented by several mathematical functions or models used (i.e. Basic cut-off, ROC curves, PCA, SVM etc.)

From the different data analysis provided with two different cohorts of patients according to Example 1 in this description, is made clear that the levels of RBP4 and NT-proBNP, and optionally of GFAP, allow good discrimination between IS and ICH and also the safe selection of a candidate for reperfusion therapy. Reference intervals or values for correct classification will be accommodated depending on several variables computed in the methods. In any case, these values will be indicated to personnel having to carry out the methods.

With these two or three markers a global image of patients that were well-classified was obtained, thus making them useful for correct classification of a test patient. Of particular interest is, moreover, that ischemic patients properly classified by using RBP4 and NT-proBNP biomarkers are those patients that will have a worse outcome.

As shown in the Table 5 below, the ischemic strokes (IS) identified using these two biomarkers are the ones that will have more mortality and they will be less independent at three months after stroke.

This is another reason to treat those patients as soon as possible with reperfusion techniques in order to avoid the fatal outcome that they will have if treated later following nowadays standard pathways.

TABLE 5

Data from analysed IS patients.

| | CATEGORIES | ALL (n = 155) | WELL CLASSIFIED (n = 31) | NOT CLASSIFIED (n = 124) | P |
|---|---|---|---|---|---|
| Modified Ranking score (mRS) at 3 Months after stroke | Asymptomatic | 10 (6.45%) | 1 (3.23%) | 9 (7.26%) | 0.0467 |
| | No significant disability | 31 (20%) | 4 (12.9%) | 27 (21.77%) | |
| | Mild disability | 24 (15.48%) | 2 (6.45%) | 22 (17.74%) | |
| | Moderate disability | 17 (10.97%) | 4 (12.9%) | 13 (10.48%) | |
| | Moderate-severe disability | 29 (18.71%) | 4 (12.9%) | 25 (20.16%) | |
| | Severe disability | 5 (3.23%) | 1 (3.23%) | 4 (3.23%) | |
| | Death | 39 (25.16%) | 15 (48.39%) | 24 (19.35%) | |
| mRS (dependence vs independence) | >2 | 90 (58.06%) | 24 (77.42%) | 66 (53.23%) | 0.0252 |
| | <=2 | 65 (41.94%) | 7 (22.58%) | 58 (46.77%) | |
| Mortality | No | 122 (78.71%) | 18 (58.06%) | 104 (83.87%) | 0.0027 |
| | Yes | 32 (20.65%) | 13 (41.94%) | 19 (15.32%) | |
| Hemorrhagic Transformation (HT) | No | 74 (47.74%) | 18 (58.06%) | 56 (45.16%) | 1 |
| | Yes | 30 (19.35%) | 7 (22.58%) | 23 (18.55%) | |
| Symptomatic HT | No | 144 (92.9%) | 29 (93.55%) | 115 (92.74%) | 1 |
| | Yes | 9 (5.81%) | 2 (6.45%) | 7 (5.65%) | |
| Sex | Male | 65 (41.94%) | 9 (29.03%) | 56 (45.16%) | 0.1544 |
| | Female | 90 (58.06%) | 22 (70.97%) | 68 (54.84%) | |
| Alcohol | No | 138 (89.03%) | 28 (90.32%) | 110 (88.71%) | 0.1668 |
| | Moderate | 6 (3.87%) | 3 (9.68%) | 3 (2.42%) | |
| | Excessive | 2 (1.29%) | 0 (0%) | 2 (1.61%) | |
| Tobacco | No | 131 (84.52%) | 28 (90.32%) | 103 (83.06%) | 1 |
| | Yes | 16 (10.32%) | 3 (9.68%) | 13 (10.48%) | |
| Hypertension | | 39 (25.16%) | 5 (16.13%) | 34 (27.42%) | 0.2773 |
| | | 115 (74.19%) | 26 (83.87%) | 89 (71.77%) | |
| Dislipidemia | No | 86 (55.48%) | 20 (64.52%) | 66 (53.23%) | 0.3527 |
| | Yes | 69 (44.52%) | 11 (35.48%) | 58 (46.77%) | |
| Diabetes | No | 108 (69.68%) | 17 (54.84%) | 91 (73.39%) | 0.0733 |
| | Yes | 47 (30.32%) | 14 (45.16%) | 33 (26.61%) | |
| PERIPHERAL ARTERIAL DISEASE | No | 146 (94.19%) | 29 (93.55%) | 117 (94.35%) | 1 |
| | Yes | 8 (5.16%) | 2 (6.45%) | 6 (4.84%) | |
| PREVIOUS STROKE | No | 122 (78.71%) | 23 (74.19%) | 99 (79.84%) | 0.6589 |
| | Yes | 33 (21.29%) | 8 (25.81%) | 25 (20.16%) | |
| CARDIOPHATY | No | 80 (51.61%) | 9 (29.03%) | 71 (57.26%) | 0.009 |
| | Yes | 75 (48.39%) | 22 (70.97%) | 53 (42.74%) | |
| Coronary artery disease | No | 131 (84.52%) | 24 (77.42%) | 107 (86.29%) | 0.3453 |
| | Yes | 24 (15.48%) | 7 (22.58%) | 17 (13.71%) | |
| EMBOLIGEN CARDIOPHATY | No | 93 (60%) | 11 (35.48%) | 82 (66.13%) | 0.0056 |
| | Major | 61 (39.35%) | 20 (64.52%) | 41 (33.06%) | |
| | Minor | 1 (0.65%) | 0 (0%) | 1 (0.81%) | |
| Atrial fibrillation | No | 102 (65.81%) | 13 (41.94%) | 89 (71.77%) | 0.0035 |
| | Yes | 53 (34.19%) | 18 (58.06%) | 35 (28.23%) | |
| NEUROLOGICAL DISEASE | No | 131 (84.52%) | 27 (87.1%) | 104 (83.87%) | 0.08677 |
| | Yes | 24 (15.48%) | 4 (12.9%) | 20 (16.13%) | |
| PREVIOUS mRS | Asymptomatic | 35 (22.58%) | 4 (12.9%) | 31 (25%) | 0.0211 |
| | No significant disability | 56 (36.13%) | 6 (19.35%) | 50 (40.32%) | |
| | Mild disability | 24 (15.48%) | 8 (25.81%) | 16 (12.9%) | |
| | Moderate disability | 24 (15.48%) | 9 (29.03%) | 15 (12.1%) | |

TABLE 5-continued

Data from analysed IS patients.

| | CATEGORIES | ALL (n = 155) | WELL CLASSIFIED (n = 31) | NOT CLASSIFIED (n = 124) | P |
|---|---|---|---|---|---|
| | Moderate-severe disability | 12 (7.74%) | 4 (12.9%) | 8 (6.45%) | |
| | Severe disability | 1 (0.65%) | 0 (0%) | 1 (0.81%) | |
| PREVIOUS | No | 115 (74.19%) | 18 (58.06%) | 97 (78.23%) | 0.0201 |
| DISABILITY | Yes | 37 (23.87%) | 13 (41.94%) | 24 (19.35%) | |
| Treatment | None | 11 (7.1%) | 1 (3.23%) | 10 (8.06%) | 0.6046 |
| | Yes | 142 (91.61%) | 29 (93.55%) | 113 (91.13%) | |
| Antiplatelets | None | 93 (60%) | 13 (41.94%) | 80 (64.52%) | 0.0483 |
| | Yes | 60 (38.71%) | 17 (54.84%) | 43 (34.68%) | |
| Anticoagulants | None | 118 (76.13%) | 19 (61.29%) | 99 (79.84%) | 0.0779 |
| | Yes | 35 (22.58%) | 11 (35.48%) | 24 (19.35%) | |
| Statins | None | 88 (56.77%) | 15 (48.39%) | 73 (58.87%) | 0.4406 |
| | Yes | 64 (41.29%) | 15 (48.39%) | 49 (39.52%) | |
| Anti Hypertensive drugs | None | 45 (29.03%) | 3 (9.68%) | 42 (33.87%) | 0.0174 |
| | Yes | 108 (69.68%) | 27 (87.1%) | 81 (65.32%) | |
| Stroke | Atherotrombotic | 21 (13.55%) | 1 (3.23%) | 20 (16.13%) | 0.1339 |
| Etiology | Cardioembolic | 83 (53.55%) | 22 (70.97%) | 61 (49.19%) | |
| (TOAST) | Lacunar | 3 (1.94%) | 1 (3.23%) | 2 (1.61%) | |
| | Other infrequent cases | 4 (2.58%) | 0 (0%) | 4 (3.23%) | |
| | Undetermined | 44 (28.39%) | 7 (22.58%) | 37 (29.84%) | |
| OCSP | PACI | 62 (40%) | 8 (25.81%) | 54 (43.55%) | 0.3238 |
| | TACI | 83 (53.55%) | 20 (64.52%) | 63 (50.81%) | |
| | POCI | 7 (4.52%) | 2 (6.45%) | 5 (4.03%) | |
| | LACI | 3 (1.94%) | 1 (3.23%) | 2 (1.61%) | |
| i.v. | No | 67 (43.23%) | 18 (58.06%) | 49 (39.52%) | 0.1038 |
| Thrombolysis | Yes | 87 (56.13%) | 13 (41.94%) | 74 (59.68%) | |
| NIHSS atadmission | | 13.86 ± 5.89 | 15.19 ± 7.51 | 13.53 5.39 | 0.31 |
| Age | | 76.17 ± 12.63 | 80.58 ± 7.56 | 75.07 ± 13.41 | 0.064 |
| Systolic BP | | 150.11 ± 25.63 | 145.75 ± 29.38 | 151.36 ± 24.48 | 0.48 |
| Dyastolic BP | | 77.86 ± 15.67 | 73.54 ± 13.48 | 79.11 ± 16.1 | 0.07 |
| Glycemia | | 140.95 ± 51.54 | 151.29 ± 51.67 | 138.32 ± 51.39 | 0.093 |
| ASPECTS score | | 9.16 ± 1.25 | 9.04 ± 1.53 | 9.19 ± 1.17 | 0.7 |

In lay terms this technology based on determination of both biomarkers increases the odds of being treated within the "golden hour" (<60 min since ischemic stroke onset) and that fact almost double the odds of becoming asymptomatic, triples the odds of being independent and increases the odds of survival fourfold. (See Kunz et al. "Effects of Ultraearly Intravenous Thrombolysis on Outcomes in Ischemic Stroke: The STEMO (Stroke Emergency Mobile) Group", Circulation-2017 May 2; 135(18):1765-1767, for more information regarding "golden hour" and therapeutic action protocols).

Example 2. Classification of Patients and Selection of Therapy in a Different Cohort of 32 Patients Data set consisted in 32 patients (18 hemorrhagic, 14 ischemic). The aim was to separate the maximum of patients in both classes without any risk of misclassification.

In order to do that, 4 different techniques for GFAP biomarkers were used. So, the procedure was computed for each different technique.

The procedure consisted in finding the best cut-off for GFAP, removing the patients that were classified with 100% sensitivity or 100% specificity and, with the rest of data (not classified/removed with GFAP, so that not perfectly classified) next cut-off with RBP4 biomarker data was computed, classifying again the patients with 100% sensitivity or 100% specificity and removing them. Finally, repeating the procedure with NT-proBNP biomarker data.

Below there are included cut-off values used for each of the techniques for GFAP determination.

GFAP DxSYS_CLIA (DxSYS Inc. chemiluminescence immunoassay): Using the cut-off>80.6 pg/ml 15 hemorrhagic patients (83% of the total hemorrhagic patients) were correctly classified.

GFAP DxSYS_TMB (DxSYS Inc using 3,3',5,5'-tetramethylbenzidine (TMB)): Using the cut-off>88.685 pg/ml 14 hemorrhagic patients (78% of the total hemorrhagic patients) were correctly classified. Same result was obtained using a cut-off of 100 pg/ml.

GFAP Quanterix®: Using cut-offs of >2066.078 pg/ml and <166.67 pg/ml 14 hemorrhagic patients and 3 ischemic patients (78% of the total hemorrhagic patients and 21.4% of ischemic patients) were correctly classified.

GFAP Elisa (Elisa kit cat #RD192072200, BioVendor): Using the cut-off>50.5 pg/ml 11 hemorrhagic patients (61.1% of the total hemorrhagic patients) were correctly classified.

After applying all these cut-offs and proceeding with RBP4 and NT-proBNP as said, finally 17/18 hemorrhagic patients and 12/14 ischemic patients were correctly classified.

Therefore, this procedure illustrated that determining the 3 biomarkers in a serial steps allows accurate classification of patients for deciding the appropriate medical regimen (reperfusion therapy in ischemic strokes). A summary of the procedure for each analytical technique is depicted in Table 6.

TABLE 6

| GFAP technique % Number of patients (hemorrhagic/ischemi; hem/isch) | GFAP pg/ml Cut-off | RBP4 µg/ml Cut-off | NT-proBNP pg/ml Cut-off | Number/% of patients NOT classified correctly using the 3 biomakers |
| --- | --- | --- | --- | --- |
| | Cut-offs of markers for correct classification |
| DxSYS-CLIA N = 32 (18/14) | >80.6/−15/0 83% hem/0% isch | −/>38.148 0/7 0% hem/50% isch | <858.45/>1682.5 2/5 11% hem/36% isch | 1/2 5.55% hem 14.3% isch |
| DxSYS-TMB N = 32 (18/14) | >88.685/−14/0 78% hem/0% isch | −/>38.148 0/7 0% hem/50% isch | <910.95/>1682.5 3/5 17% hem/36% isch | 1/2 5.55% hem 14.3% isch |
| DxSYS-TMB N = 32 (18/14) | >100/−14/0 78% hem/0% isch | −/>38.148 0/7 0% hem/50% isch | <910.95/>1682.5 3/5 17% hem/36% isch | 1/2 5.55% hem 14.3% isch |
| Quanterix N = 32 (18/14) | >2066.078/<166.67 14/3 78% hem/21.4% isch | −/>38.1747 0/5 0% hem/35.7% isch | <910.95/>3043 3/4 16.7% hem/28.6% isch | 1/2 5.55% hem 14.3% isch |
| Biovendor-ELISA N = 32 (18/14) | >50.5/−11/0 61.1% hem/0% isch | −/>38.148 0/7 0% hem/50% isch | <910.95/>1682.5 6/7 33.3% hem/35.7% isch | 1/2 5.55% hem 14.3% isch |

Example 3. the Combination of Biomarkers with Clinical Data Improves the Accuracy of the Identification of Ischemic Strokes that Require Reperfusion Therapies An analysis of the data with the following patients and cutoffs was performed:

Hemorrhagic n=35 and Ischemic n=155

The three biomarkers in combination using the cutoffs GFAP (pg/ml)<97.03 and NT-proBNP (pg/ml)>4076.50 and RBP-4 (µg/ml) >52.52 showed a sensitivity of 0.32, a specificity of 1.00 (100%), a positive predictive value (PPV) of 1.00 and a negative predictive value (NPV) of 0.25.

When clinical data were added on top of that (specially blood pressure and glucose level), the sensitivity was improved keeping the 100% specificity. In fact, GFAP (pg/ml)<97.03 and NT-proBNP (pg/ml)>4076.50 and systolic blood pressure (SBP) mmhg<119.00, and diastolic blood pressure (DBP) (mmhg)<60.50 and RBP-4 (ug/ml) >52.52 and glycemia (mg/dl)<83.50 had a sensitivity of 0.45, and a specificity of 1.00, with PPV=1.00 and NPV=0.29.

Logistic Regression-Based Models

In order to find a feasible transformation for the data that can enhance classification precision and robustness while limiting over-fitting, several Multiple Logistic Regression Models were tested on pooled data from both cohorts (original cohort 1 n=189 of Example 1 and a replication cohort n=300 with Hemorrhagic, n=51 and Ischemic, n=249). Tested models included the panel of markers and relevant clinical variables. A model was selected by Akaike Information Criteria and used to classify individuals between Ischemic and Hemorrhagic strokes.

The chosen model contained the logarithmic transformation of GFAP (pg/ml), NT-proBNP (pg/ml) and diastolic blood pressure (mmhg) as significative predictors of Ischemic stroke condition, in the following combination:

$$-1.56 \log(GFAP(pg/ml))+0.0008 \text{ NT-proBNP (pg/ml)}-0.041 \text{ DBP (mmhg)}$$

This linear combination yielded an estimated logarithmic odds ratio score that could be treated as a compound marker. A threshold could be located in this score that maximized the desired sensitivity and specificity requirements to classify individuals between the two groups.

The weighting and aggregation of markers improved classification sensitivity over raw markers for both cohorts, when specificity was above 95%.

In the original cohort the application of this model had a sensitivity=0.60, specificity=1.00 and accuracy=0.68.

Figure 4:
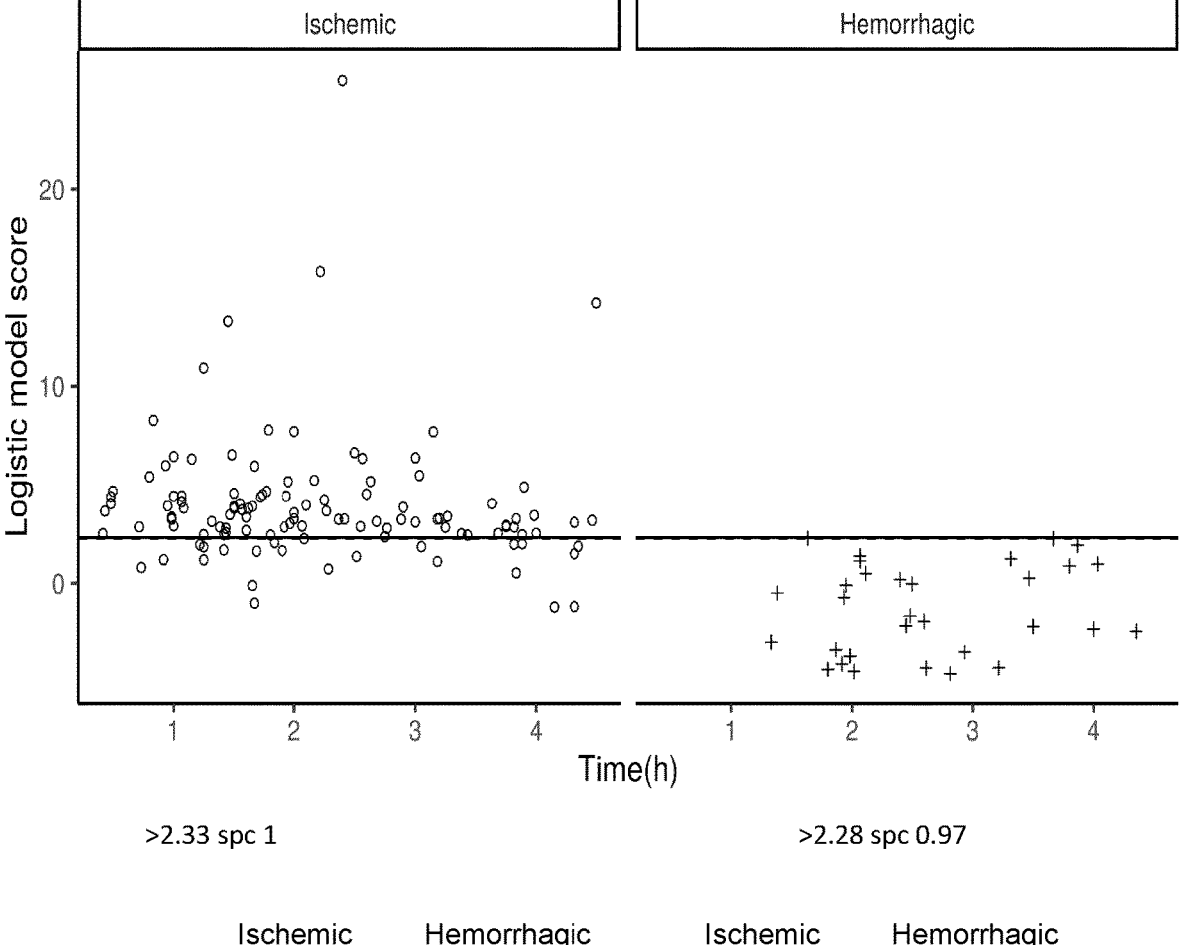
FIG. 4 is a graphic showing the classification of a cohort of subjects using a logistic model score including the logarithmic transformation of GFAP (pg/ml), NT-proBNP (pg/ml) and diastolic blood pressure (mmhg) as significative predictors of Ischemic stroke condition.

FIG. 4 illustrates graphically the classification of the subjects using this logistic model score.

Replication cohort (n=300) characteristics are listed below:

Blood samples were obtained within 3 hours of stroke onset in cases of stroke suspicion (ischemic or hemorrhagic strokes). Diagnostic and therapeutic workup was similar to the initial cohort 1 of Example 1 of studied patients used in these files in several examples (n=189).

| | Overall (N = 300) |
| --- | --- |
| Stroke | |
| Hemorrhagic | 51 (17.0%) |
| Ischemic | 249 (83.0%) |
| Mimic | 0 (0.0%) |
| Control | 0 (0.0%) |
| Sex | |
| Male | 166 (55.3%) |
| Female | 134 (44.7%) |
| Age | |
| N | 300 |
| min | 26.000 |
| max | 95.000 |
| mean | 74.187 |
| median | 77.000 |
| sd | 12.519 |
| IQ range | 67.000, 84.000 |

-continued

-continued

| | Overall (N = 300) |
|---|---|
| Alcohol abuse | |
| no | 282 (94.0%) |
| yes | 18 (6.0%) |
| Smokers | |
| no | 260 (86.7%) |
| yes | 40 (13.3%) |
| Dyslipidemia | |
| no | 143 (47.7%) |
| yes | 157 (52.3%) |
| Diabetes Mellitus | |
| no | 225 (75.0%) |
| yes | 75 (25.0%) |
| Coronariopathy | |
| no | 258 (86.0%) |
| yes | 42 (14.0%) |
| Diastolic blood pressure (mmhg) | |
| N | 284 |
| min | 25.000 |
| max | 165.000 |
| mean | 84.764 |
| median | 84.000 |
| sd | 19.915 |
| IQ range | 71.750, 95.250 |
| Systolic blood pressure (mmhg) | |
| N | 285 |
| min | 83.000 |
| max | 313.000 |
| mean | 158.340 |
| median | 156.000 |
| sd | 31.720 |
| IQ range | 138.000, 175.000 |
| Glycemia (mg/dl) | |
| N | 298 |
| min | 64.000 |
| max | 318.000 |
| mean | 135.628 |
| median | 124.000 |
| sd | 43.014 |
| IQ range | 107.250, 149.750 |
| Death (at 3 m) | |
| missing | 51 |
| No | 191 (76.7%) |
| Yes | 58 (23.3%) |
| Time from stroke onset (h) | |
| N | 300 |
| min | 0.417 |
| max | 2.500 |
| mean | 1.586 |
| median | 1.575 |
| sd | 0.474 |
| IQ range | 1.233, 2.000 |
| Previous Stroke | |
| No | 248 (82.7%) |
| Yes | 52 (17.3%) |
| Vessel Occlusion | |
| missing | 90 |
| No | 87 (41.4%) |
| Yes | 123 (58.6%) |
| Occlusion location | |
| missing | 90 |
| ACA | 1 (0.5%) |
| MCA_M1 | 65 (31.0%) |
| MCA_M2 | 24 (11.4%) |
| BA | 1 (0.5%) |

| | Overall (N = 300) |
|---|---|
| ICA | 7 (3.3%) |
| No | 87 (41.4%) |
| Tandem | 10 (4.8%) |
| TICA | 12 (5.7%) |
| VA | 3 (1.4%) |
| Baseline NIHSS score | |
| N | 300 |
| min | 5.000 |
| max | 42.000 |
| mean | 14.403 |
| median | 14.000 |
| sd | 6.624 |
| IQ range | 8.000, 20.000 |
| NIHSS score at 24 hours | |
| N | 273 |
| min | 0.000 |
| max | 42.000 |
| mean | 9.300 |
| median | 7.000 |
| sd | 7.961 |
| IQ range | 2.000, 16.000 |
| Previous mRS | |
| N | 299 |
| min | 0.000 |
| max | 5.000 |
| mean | 0.997 |
| median | 0.000 |
| sd | 1.322 |
| IQ range | 0.000, 2.000 |
| Discharge mRS | |
| N | 291 |
| min | 0.000 |
| max | 6.000 |
| mean | 3.330 |
| median | 4.000 |
| sd | 1.935 |
| IQ range | 2.000, 5.000 |
| 3 months mRS | |
| N | 239 |
| min | 0.000 |
| max | 6.000 |
| mean | 3.054 |
| median | 3.000 |
| sd | 2.148 |
| IQ range | 1.000, 5.000 |
| ASPECTS | |
| N | 248 |
| min | 0.000 |
| max | 10.000 |
| mean | 9.234 |
| median | 10.000 |
| sd | 1.474 |
| IQ range | 9.000, 10.000 |
| TOAST | |
| missing | 52 |
| Atherotrombotic | 32 (12.9%) |
| Cardioembolic | 127 (51.2%) |
| Small vessel disease | 7 (2.8%) |
| Other infrequent cases | 5 (2.0%) |
| Undetermined | 77 (31.0%) |
| OCSP | |
| missing | 65 |
| TACI | 144 (61.3%) |
| PACI | 73 (31.1%) |
| LACI | 9 (3.8%) |
| POCI | 9 (3.8%) |

-continued

| | Overall (N = 300) |
|---|---|
| tPA | |
| missing | 1 |
| No | 153 (51.2%) |
| Si | 146 (48.8%) |
| Thrombectomy | |
| missing | 1 |
| No | 264 (88.3%) |
| Si | 35 (11.7%) |
| NT-proBNP (pg/ml) | |
| N | 300 |
| min | 5.003 |
| max | 47572.018 |
| mean | 1424.552 |
| median | 445.880 |
| sd | 3889.609 |
| IQ range | 154.870, 1277.597 |
| RBP4 (ug/ml) | |
| N | 300 |
| min | 8.566 |
| max | 87.304 |
| mean | 28.112 |
| median | 26.158 |
| sd | 10.867 |
| IQ range | 20.846, 32.397 |
| GFAP (pg/ml) | |
| N | 289 |
| min | 34.782 |
| max | 6853.122 |
| mean | 682.851 |
| median | 219.673 |
| sd | 1503.459 |
| IQ range | 131.895, 370.360 |
| ddi_ngml | |
| N | 296 |
| min | 4.540 |
| max | 8.230 |
| mean | 7.004 |
| median | 6.990 |
| sd | 0.797 |
| IQ range | 6.428, 7.500 |

Example 4. Improved Accuracy to Detect Ischemic
Stroke Patients Candidates for Reperfusion
Therapies in Ultra Early Time-Points In the original cohort 1 of Example 1 (n=189) the performance of the biomarkers was evaluated in relationship with the time of blood collection from symptoms onset. Surprisingly the sooner the test was done the better that accuracy of the test:

(i) From 0 to 2 hours (Hemorrhagic n=11 and Ischemic n=82)
GFAP (pg/ml)<175.85 and NT-proBNP (pg/ml)>3916.50 and RBP-4 (ug/ml)>38.15. Sensitivity=0.70, Specificity=1.00, PPV=1.00 and NPV 0.31.
(ii) From 2 to 3 h (Hemorrhagic n=13 and Ischemic n=35)
GFAP (pg/ml)<94.37 and NT-proBNP (pg/ml)>1289.50 and RBP-4 (ug/ml)>46.55. Sensitivity=0.60, Specificity=1.00, PPV=1.00 and NPV 0.48.
(iii) From 3 to 4.5 hours (Hemorrhagic n=11 and Ischemic n=38)
GFAP (pg/ml)<98.96 and NT-proBNP (pg/ml)>4254.50 and RBP-4 (ug/ml)>53.34. Sensitivity=0.34, Specificity=1.00, PPV=1.00 and NPV 0.31.
In the replication cohort (n=300, Hemorrhagic, n=51 and Ischemic, n=249), those patients arriving very early at the hospital were selected, with blood samples obtained within the first hour of stroke onset. There were Hemorrhagic n=8 and Ischemic n=33.

In that subcohort, GFAP (pg/ml)<300.03 and NT-proBNP (pg/ml)>1033.01 and RBP-4 (ug/ml)>32.93 had an excellent accuracy, with a sensitivity=0.91, specificity=1.00, PPV=1.00 and NPV 0.73.

That was even improved and the test behaved perfect when adding some clinical variables (clinical parameters): GFAP (pg/ml)<300.03 and DSP (mmhg)<82.00 and SBP (mmhg)<143.00 and NT-proBNP (pg/ml)>2741.31 and glycemia (mgdl)<108.00. This combination gave a sensitivity=1.00, a specificity=1.00, a PPV=1.00 and a NPV 1.00.

Logistic regression was also performed in this cohort of patients with samples obtained in the first hour of symptoms onset.

The chosen model contains the logarithmic transformation of GFAP (pg/ml), NT-proBNP (pg/ml) and diastolic blood pressure (mmhg) as significative predictors of Ischemic stroke condition, in the following combination:

$$-1.56 \log(\text{GFAP(pg/ml)}) + 0.0008 \text{ NT-proBNP (pg/ml)} - 0.041 \text{ DBP (mmhg)}$$

This linear combination yielded an estimated logarithmic odds ratio score that could be treated as a compound marker. The application of this model to those patients of the replication cohort attended within the first hour of stroke onset the model had a sensitivity=0.79, specificity=1.00 and accuracy=0.83.

Figure 5:
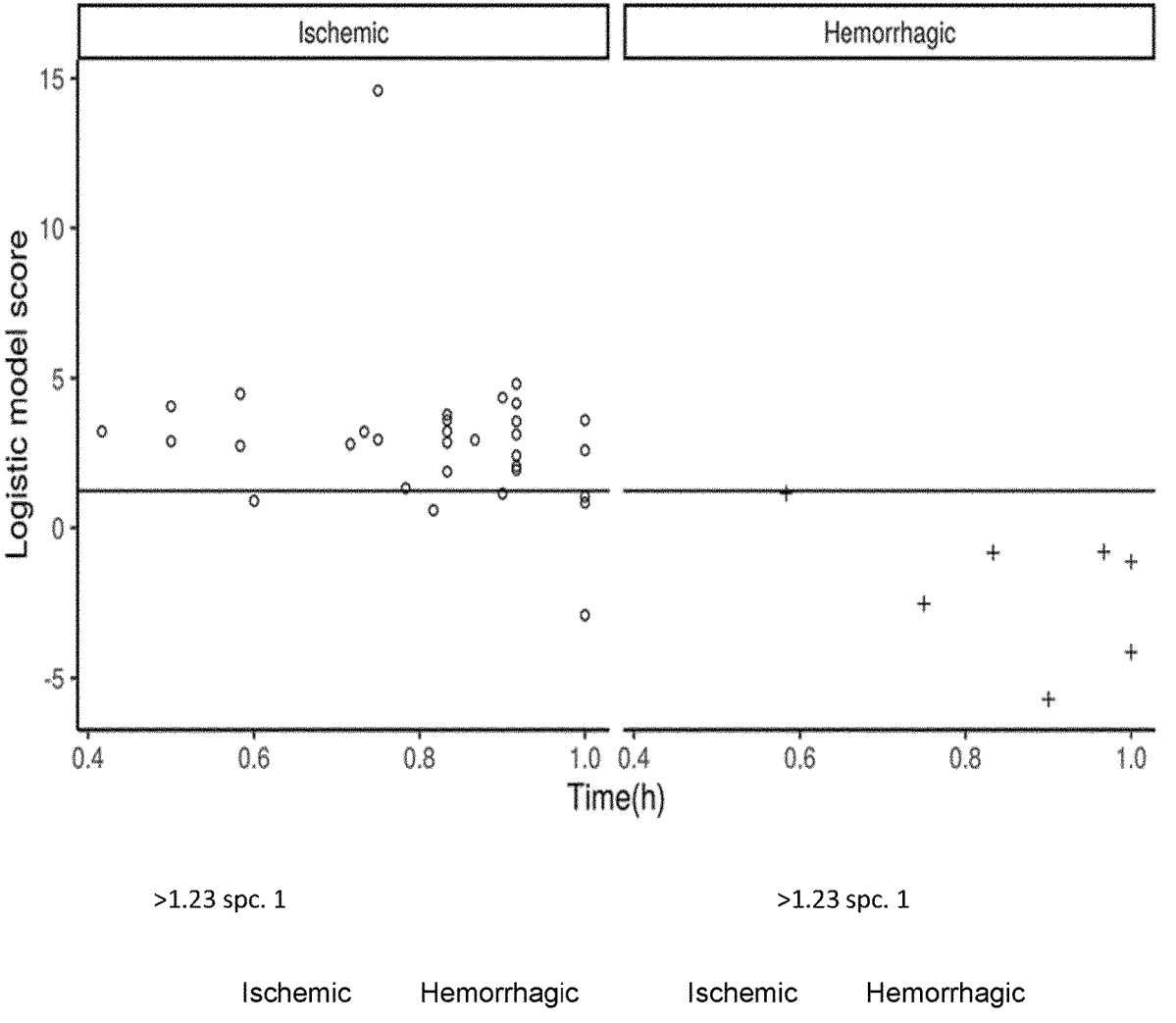
FIG. 5 is a graphic showing the classification of a cohort of subjects, in which determination of the levels of markers was performed within the first hour after stroke symptoms onset, and using a logistic model score including the logarithmic transformation of GFAP (pg/ml), NT-proBNP (pg/ml) and diastolic blood pressure (mmhg) as significative predictors of Ischemic stroke condition.

FIG. 5 illustrates graphically the classification of the subjects using this logistic model score, with data of isolated samples within the first hour after onset of stroke.

All these data in Example 4 demonstrate that, selected biomarkers RBP4, NT-proBNP and GFAP allow high sensitivities if they can be measured soon after the onset of stroke. In particular if they can be determined within the first and second hour after the onset.

That a better sensitivity can be achieved for a fixed specificity the sooner the test is performed is a surprising effect in stroke, where generally the biomarkers give an appropriate signal after a longer period after onset. Far from being a disadvantage, this is a goal in this pathology because a good and a reliable classification of patients can be fast done in the critical period of the disease (for example at ambulance level). This allows taking the best and most adequate decision at those critical moments, which can later be verified with additional biomarkers (for example once the patient arrives to hospital).

Example 5. A Rapid Point-of-Care Blood Test
Performed at the Ambulances to Select Ischemic
Stroke Patients that Deserve Reperfusion Therapies
from any Other Disease that Resembles an Acute
Ischemic Stroke (Stroke Mimicking Conditions and
Intracerebral Hemorrhages)

The panel of biomarkers included in this invention (RBP4, NT-proBNP and GFAP) was validated using a Point-of-Care test (POCT) for the ambulances which may identify those with an ischemic stroke using a blood sample in order to start reperfusion therapies at the ambulance (thrombolysis) or sending this patients to the right hospital in order to get the best reperfusion therapy (thrombolysis or mechanical thrombectomy).

Methods

Patients with suspected stroke (<6 hours) were enrolled within the BIO-FAST study (Biomarkers for Initiating Onsite and Faster Ambulance Stroke Therapies) by a network of more than 20 ambulances and helicopters in the region of Seville at the south of Spain. Blood samples were collected by the ambulances that used a rapid POCT (10 to 15 minutes until the results is given) to measure RBP-4/NT-pro-BNP and GFAP was measured by SIMOA-Quanterix technology.

Inclusion criteria: Patients>18 years old; Stroke code activated by the coordinator center and <6 hours from symptoms onset. In the case of stroke with uncertain chronology or wake-up stroke, the initial time will be considered as the last moment the patient was seen fine.

Exclusion criteria: Prehospital diagnosis different of stroke; Impossibility of getting a prehospital blood sample and Refusal to provide the informed consent by the patient/relative. Type of samples Extraction of one EDTA tube of blood sample (10 mL) for biobank+one EDTA tube of blood sample (2 mL) for POCs. The samples were included in the collection placed in Vail d'Hebron hospital in the registered collection with code C.0003176 according to the established requirements in the RD 1716/2011, until they are fully used for biomarkers discovery research.

RBP4 rapid test. RBP4 POC lateral flow dispositive.

NT-proBNP rapid test. Nt-proBNP POC lateral flow dispositive.

GFAP SIMOA-Quanterix technology

Results 20 patients were included (10 were ischemic strokes, 3 intracerebral hemorrhages and 7 stroke-mimicking conditions). To run the POCT at the ambulance is feasible and even one case was performed in the helicopter with no incidences.

The rapid POCT (RBP-4-NT-proBNP) with selected cutoffs for these biomarkers identified precisely 50% of IS without misclassifying any ICH or mimics (100% specificity, 50% sensitivity). When wake-up-strokes were excluded the POCT identified precisely 62.5% of IS without misclassifying any ICH or mimics (100% specificity, 62.5% sensitivity).

Using the blood samples stored from those patients, GFAP was measured using SIMOA-Quanterix technology in order to explore how that might improve the results with a POCT that might incorporate GFAP, RBP-4 and NT-proBNP. There were identified four patients with very elevated GFAP levels, two were ICH, one was an IS and one mimic. Ruling out those four cases allowed to increase sensitivity to more than 70% maintaining the specificity at 100%.

20% of IS might have been treated within the first 30 min from symptoms onset using the POCT. Moreover, one mimic that received tPA might have been avoided since the POCT was negative for IS. tPA treated patients might had get the drug 1 h 30 min before by using the test at the ambulance-3 ischemic patients (30%) might had been into the 4.5 h time window for the test and were out of that time when the CT scan was performed at the hospital.

Conclusions

The panel of biomarkers including RBP-4, NT-proBNP and GFAP provides useful sensitivity rates at 100% specificity for ischemic strokes. This might change standard clinical practice by using a POCT that allows initiating pre-hospital reperfusion therapies in selected cases much faster than using standard technologies.

The data obtained with POCT allowing determining levels in blood of RBP4 and NT-proBNP, and further completed with the GFAP determination, supposed a first test in real-life conditions, in which patients with IS and ICH should be screened within the existing presence of mimics (non-stroke patients with stroke-like symptomatology). In this real scenario, even sensitivity was higher (more than 50%) than in some of the previous Examples, while fixing a 100% of specificity. This is an unexpected advantage of the panel of biomarkers to be added to the one that they allow a good and reliable classification, which is translated to an appropriate selection of therapy that can be administered before getting a hospital.

Example 6. RBP-4, NT-proBNP and GFAP Identify Ischemic Stroke Patients with Large Vessel Occlusion (LVO) that are the Ones that Require Mechanical Thrombectomy and Need to be Transferred to a Reference Center with this Therapy Available The identification of LVO in the two cohorts of stroke patients previously disclosed (n=189 and n=300) was based on the presence and location of an occluded brain artery in CT angiography (CTA) performed at hospital arrival. A restrictive definition of LVO was followed that was described as occlusion of any of the following arteries or arterial segments: occlusion of the intracranial carotid (ICA), basilar (BA), and M1 segment of middle cerebral artery occlusions.

(See. Vanacker P, Heldner M R, Amiguet M, et al. Prediction of large vessel occlusions in acute stroke: National institute of Health Stroke Scale is hard to beat. Crit Care Med 2016; 44:e336-43).

The same biomarkers showed below are also useful to identify LVO with less strict criteria that includes also occlusion in more distal parts of the middle cerebral artery (MCA) such as M2 (LVO defined as occlusion of the ICA, M1, M2, or BA), just by using different cutoffs.

A.—INITIAL COHORT 1 of Example 1 (N=189):

Prediction of patients with LVO (134 no LVO vs 56 LVO):

GFAP (pg/ml)<694.48 and NT-proBNP (pg/ml)>1764.50 and RBP-4 (µg/ml)>35.22 had a sensitivity=0.98, specificity=0.18, PPV=0.33 and NPV 0.96; that was improved when adding clinical and laboratory variables such as baseline NIHSS score>11 points and d-dimer (ng/ml)>1432.43 that had a sensitivity=1.00, a specificity=0.46, a PPV=0.43 and a NPV 1.00.

When blood samples were obtained within 2 hours of symptoms onset it was baseline NIHSS score>11 points and RBP-4 (ug/ml)>51.53 the markers that better performed with a sensitivity=1.00, a specificity=0.40, a PPV=0.46 and a NPV 1.00.

Moreover, among those the ones that get a thrombectomy performed (165 no thrombectomy and 22 thrombectomies) the biomarkers GFAP (pg/ml)>209.43 and NT-proBNP (pg/ml)<848.15 had a sensitivity=1.00, a specificity=0.23, a PPV=0.15 and NPV 1.00. This was improved when adding clinical variables such as baseline NIHSS score>11 points and GFAP (pg/ml)<54.84 having a sensitivity=1.00, specificity=0.43, PPV=0.19 and NPV 1.00.

When blood samples were obtained within 2 hours of symptoms onset it was NT-proBNP with d-dimer the ones that performed better with a sensitivity=1.00, a specificity=0.70, a PPV=0.39 and a NPV 1.00.

B.—Replication Cohort (n=300)

LVO (restrictive definition) No LVO=215 vs LVO=85

The biomarkers GFAP (pg/ml)<153.18 and NT-proBNP (pg/ml)>692.60 and RBP-4 (μg/ml)<39.72 showed a sensitivity=1.00, a specificity=0.09, a PPV=0.30 and a NPV 1.00. Those results improved by adding clinical data baseline NIHSS score>11 points and RBP-4 (ug/ml)<29.03 and glycemia (mg/dl)<71.50, that showed a sensitivity=1.00, specificity=0.20, PPV=0.33 and NPV 1.00.

Those results were even better for baseline NIHSS score and RBP-4 when blood samples were obtained within 2 hours after onset, having a sensitivity=1.00, a specificity=0.45, a PPV=0.43 and a NPV 1.00.

Among those who got a thrombectomy (no thrombectomy n=264 and thrombectomy n=35) the biomarkers GFAP (pg/ml)<153.18 and NT-proBNP (pg/ml)<2049.01 had a sensitivity=1.00, a specificity=0.14, a PPV=0.13 and a NPV 1.00 to correctly identify those patients. That improved by adding clinical and laboratory variables, since then GFAP (pg/ml)<153.18 and d-dimer (ng/ml)>7.29 and diastolic blood pressure (mmhg)>89.50 were having a sensitivity=0.97, a specificity=0.33, a PPV=0.16 and a NPV 0.99.

CITATION LIST

Patent Literature

WO2016087611

Non Patent Literature

Reynolds et al., "Early Biomarkers of Stroke", Clinical Chemistry-2003, vol.: 49 (10), pp.: 1733-1739

Montaner et al. "Etiologic Diagnosis of Ischemic Stroke Subtypes With Plasma Biomarkers", Stroke 2008, vol. no. 39, pp.: 2280-2287

Adams H P Jr Neurology. 1999 Jul. 13; 53(1): 126-31.

Tsivgoulis G. et al, Neurology. 2014 Sep. 19

BLASTManual, Altschul, S., et al, NCBI NLM NIH Bethesda, Md. 20894, Altschul, S., et al, J. Mol. Biol. 215: 403-410 (1990)

Jolliffe, I. T. (2002). Principal Component Analysis, second edition (Springer), ISBN 0-387-95442-2.

Kunz et al. "Effects of Ultraearly Intravenous Thrombolysis on Outcomes in Ischemic Stroke: The STEMO (Stroke Emergency Mobile) Group", Circulation-2017 May 2; 135(18):1765-1767.

Vanacker P, Heldner M R, Amiguet M, et al. Prediction of large vessel occlusions in acute stroke: National institute of Health Stroke Scale is hard to beat. Crit Care Med 2016; 44:e336-43.

Rai A T et al. (2017). A population-based incidence of acute large vessel occlusions and thrombectomy eligible patients indicates significant potential for growth of endovascular stroke therapy in the USA. J Neurointery Surg. 9:722-6.

Crowe R P, Myers J B, Fernandez A R, Bourn S, McMullan J T. Prehosp Emerg Care. 2020 Feb. 25:1-9.

Gandhi C D, Al Mufti F, Singh iP, et al. Neuroendovascular management of emergent large vessel occlusion: update on the technical aspects and standards of practice by the Standards and Guidelines Committee of the Society of Neurointerventional Surgery. J Neurointery Surg 2018; 10:315-20).

Lakomkin N, Dhamoon M, Carroll K, et al. Prevalence of large vessel occlusion in patients presenting with acute ischemic stroke: a 10-year systematic review of the literature. J Neurointery Surg 2019; 11:241-5.

Waqas M, et al. Effect of definition and methods on estimates of prevalence of large vessel occlusion in acute ischemic stroke: a systematic review and meta-analysis. J Neurointery Surg. 2020 March; 12(3):260-265

---

The invention claimed is:

1. A method for diagnosing and treating large vessel occlusion (LVO) in a patient, said method comprising:
    (a) determining the levels of RBP4 and of NT-proBNP in an isolated sample of a subject;
    (b) comparing the levels of RBP4, and of NT-proBNP with a corresponding reference value, wherein said reference value or interval is selected from a value or interval of values from a reference subject suffering from LVO,
    (c) diagnosing the patient with LVO when at least the levels of RBP4 and NT-proBNP are both within the value or interval of values from the reference subject suffering from LVO; and
    (d) administering a reperfusion therapy comprising mechanical thrombectomy to the diagnosed patient.

2. The method according to claim 1, further comprising determining the level of glial fibrillary acid protein (GFAP) in the isolated sample.

3. The method according to claim 1, further comprising measuring one or more clinical parameters selected from blood pressure, glycemia, levels of blood d-dimer, age, scores from systematic assessment tools of stroke-related neurologic deficits, gender, and combinations thereof.

4. The method according to claim 1, wherein the reperfusion therapy comprises first administering an antithrombotic agent to the patient followed by mechanical thrombectomy.

5. The method according to claim 1, comprising determining the levels of RBP4, NT-proBNP, GFAP, and, d-dimer.

6. A method for diagnosing and treating large vessel occlusion (LVO) in a subject, the method comprising:
    (a) determining the levels of GFAP and d-dimer in an isolated sample of a subject and determining blood pressure of the subject;
    (b) comparing the levels of GFAP, d-dimer, and blood pressure with a corresponding reference value, wherein said reference value or interval is selected from a value or interval of values from a reference subject suffering from LVO,
    (c) diagnosing the subject with LVO when at least the levels of GFAP, d-dimer, and blood pressure are within the value or interval of values from the reference subject suffering from LVO; and
    (d) administering a reperfusion therapy comprising mechanical thrombectomy to the diagnosed subject.

* * * * *